United States Patent
Charneau et al.

(10) Patent No.: US 9,238,824 B2
(45) Date of Patent: *Jan. 19, 2016

(54) LENTIVIRAL TRIPLEX DNA, AND VECTORS AND RECOMBINANT CELLS CONTAINING LENTIVIRAL TRIPLEX DNA

(71) Applicants: INSTITUT PASTEUR, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Pierre Charneau, Paris (FR); Veronique Zennou, New York, NY (US); Francoise Pflumio, Vitry-sur-Seine (FR); Aude Sirven, Paris (FR); Anne Dubart Kupperschmitt, Choisy-le-Roi (FR)

(73) Assignees: Institut Pasteur, Paris (FR); Institut National de la Santé et de la Recherche Médicale, Paris (FR); Centre National de la Recherche Scientifique, Paris (FR)

( * ) Notice: Subject to any disclaimer, the term of this patent is extended or adjusted under 35 U.S.C. 154(b) by 244 days.

This patent is subject to a terminal disclaimer.

(21) Appl. No.: 13/942,180

(22) Filed: Jul. 15, 2013

(65) Prior Publication Data
US 2015/0011006 A1  Jan. 8, 2015

Related U.S. Application Data

(63) Continuation of application No. 13/301,147, filed on Nov. 21, 2011, now Pat. No. 8,512,993, which is a continuation of application No. 11/291,390, filed on Dec. 1, 2005, now Pat. No. 8,093,042, which is a continuation of application No. 09/685,343, filed on Oct. 11, 2000, now abandoned.

(60) Provisional application No. 60/158,387, filed on Oct. 12, 1999.

(51) Int. Cl.
| C12N 15/86 | (2006.01) |
| C12N 15/64 | (2006.01) |
| C12N 7/00 | (2006.01) |
| A61K 48/00 | (2006.01) |

(52) U.S. Cl.
CPC ............ *C12N 15/86* (2013.01); *A61K 48/0066* (2013.01); *C12N 7/00* (2013.01); *A61K 48/00* (2013.01); *C12N 2740/15043* (2013.01); *C12N 2740/16042* (2013.01); *C12N 2740/16111* (2013.01); *C12N 2740/16211* (2013.01); *C12N 2740/16311* (2013.01); *C12N 2830/60* (2013.01)

(58) Field of Classification Search
CPC .............................. C12N 15/86; C12N 15/64
See application file for complete search history.

(56) References Cited

U.S. PATENT DOCUMENTS

| 6,682,907 | B1 | 1/2004 | Charneau et al. |
| 7,968,332 | B2 | 6/2011 | Charneau et al. |
| 7,981,671 | B2 | 7/2011 | Charneau et al. |
| 8,093,042 | B2 | 1/2012 | Charneau et al. |
| 8,349,606 | B2 | 1/2013 | Charneau et al. |
| 8,367,068 | B2 | 2/2013 | Charneau et al. |
| 8,450,087 | B2 | 5/2013 | Charneau et al. |
| 8,460,678 | B2 | 6/2013 | Charneau et al. |
| 2003/0072938 | A1 | 4/2003 | Kappes et al. |
| 2003/0194392 | A1 | 10/2003 | Charneau et al. |
| 2004/0081636 | A1 | 4/2004 | Charneau et al. |
| 2006/0040347 | A1 | 2/2006 | Charneau et al. |
| 2007/0087354 | A1 | 4/2007 | Charneau et al. |
| 2007/0224679 | A1 | 9/2007 | Charneau et al. |
| 2010/0028382 | A1 | 2/2010 | Charneau et al. |
| 2010/0221820 | A1 | 9/2010 | Charneau et al. |
| 2011/0206710 | A1 | 8/2011 | Despres et al. |
| 2012/0122204 | A1 | 5/2012 | Charneau et al. |

(Continued)

FOREIGN PATENT DOCUMENTS

| EP | 1 092 779 A1 | 4/2001 |
| FR | 2 777 909 A1 | 10/1999 |

(Continued)

OTHER PUBLICATIONS

Case et al., "Stable Transduction of Quiescent CD34+ CD38– Human Hematopoietic Cells by HIV-1-Based Lentiviral Vectors", Proc. Natl. Acad. Sci USA 96:2988-2993, Mar. 1999.

Evans et al., "Human Cord Blood CD34+ CD38– Cell Transduction via Lentivirus-Based Gene Transfer Vectors", Human Gene Therapy 10:1479-1489, Jun. 10, 1999.

Miyoshi et al., "Transduction of Human CD34+ Cells That Mediate Long-Term Engraftment of NOD/SCID Mice by HIV Vectors", Science 283(5402):682-685, Jan. 29, 1999.

(Continued)

*Primary Examiner* — J. E. Angell
(74) *Attorney, Agent, or Firm* — Law Office of Salvatore Arrigo and Scott Lee, LLP

(57) ABSTRACT

The present invention provides nucleic acid, vectors, viruses, and recombinant cells comprising triple-stranded structures, such as those resulting from central initiation and termination of HIV-1 reverse transcription at the center of HIV-1 linear DNA genomes. These triplex structures can act as a cis-determinant of HIV-1 DNA nuclear import, allowing infection of non-dividing target cells. In one aspect, the presence of the DNA triplex sequence in an HIV vector strongly stimulates gene transfer in hematopoietic stem cells. The invention also provides methods of using these triplex structures for making recombinant cells, as well as methods of using the recombinant cells to express proteins of interest both in vitro and in vivo.

20 Claims, 16 Drawing Sheets

(56) References Cited

U.S. PATENT DOCUMENTS

| | | | |
|---|---|---|---|
| 2012/0122963 | A1 | 5/2012 | Charneau et al. |
| 2013/0157357 | A1 | 6/2013 | Charneau et al. |

FOREIGN PATENT DOCUMENTS

| | | |
|---|---|---|
| WO | WO 97/12622 A1 | 4/1997 |
| WO | WO 98/46083 A1 | 10/1998 |
| WO | WO/99/55892 A1 | 11/1999 |
| WO | WO 00/31280 A2 | 6/2000 |

OTHER PUBLICATIONS

Naldini et al., In Vivo Gene Delivery and Stable Transduction of Nondividing Cells by a Lentiviral Vector:, Science 272:263-267, Apr. 12, 1996.

Uchida et al., "HIV, But Not Murine Leukemia Virus, Vectors Mediate High Efficiency Gene Transfer Into Freshly Isolated G0/G1 Human Hematopoietic Stem Cells", Proc. Natl. Acad Sci, USA, 95:11939-11944, Sep. 1998.

Zufferey et al., Multiply Attenuated Lentiviral Vector Achieves Efficient Gene Delivery in Vivo:, Nature Biotechnology 15(9):871-875, Sep. 1997.

Charneau et al., "HIV-1 Reverse Transcription", J. Mol. Bol. 241 (5):651-662, Sep. 1994.

Stetor et al., "Characterization of (+) Strand Initiation and Termination Sequences Located at Center of the Equine Infectious Anemia Virus Genome", Biochemistry 38:3656-3667, Mar. 1999.

Zennou et al., "HIV-1 Genome Nuclear Import is Mediated by a Central DNA Flap", Cell, 101(2):173-185, Apr. 14, 2000.

Sirven et al., The Human Immunodeficiency Virus Type-1 Central DNA Flap is a Crucial Determination for Lentiviral Vector Nuclear Import and Gene Transduction of Human Hematopoietic Stem Cells:, Blood 96(13):4103-4110, Dec. 15, 2000.

European Patent Office, International Search Report, PCT/EP00/10418, Jun. 8, 2001.

Vile et al., Cancer Gene Therapy: Hard Lessons and New Courses, 2000, Gene Therapy, vol. 7, pp. 2-8.

Patterson, A Statement of Amy Patterson, M.D. of the National Institutes of Health, Department of Health and Human Services, 2000, pp. 1-9.

Eck et al., Gene-Based Therapy, 1996, The Pharmaceutical Basis of Therapeutics, vol. 9, pp. 77-101.

Verma et al., Gene Therapy-Promises, Problems and Prospects, 1997, Nature, vol. 389, pp. 239-242.

Hanazono et al., Gene Transfer into Nonhuman Primate Hematopoietic Stem Cells; Implications for Gene Therapy, 2001, Stem Cells, vol. 19. pp. 12-23.

Deonarain et al., Ligand-Targeted Receptor-Mediated Vectors for Gene Delivery, 1998, EEP. Opin. Ther. Patents, vol. 8, pp. 53-69.

Akkina et al., High-Efficiency Gene Transfer into CD34+ Cells with a Human Immunodeficiency Virus Type 1-Based Retroviral Vector Pseudotyped with Vesicular Stomatitis Virus Envelope Glycoprotein G, vol. 70, No. 4, pp. 2581-2585 (1996).

Naldini et al., Efficient Transfer, Integration, and Sustained Long-Term Expression of the Transgene in Adult Rat Brains Injected with a Lentiviral Vector. Proc. Nat'l Acad. Sci., vol. 93, pp. 11382-11388 (1996).

Mullins et al., Transgenesis in Nonmurine Species, Hypertension 1993, 22:630-633.

Mullins et al., Transgenesis in the Rat and Large Mammals, J. Clin. Invest. 97:1557-1560 (1996).

Cameron et al., Recent Advances in Transgenic Technology, Mol. Biotechnology &:253-265 (1997).

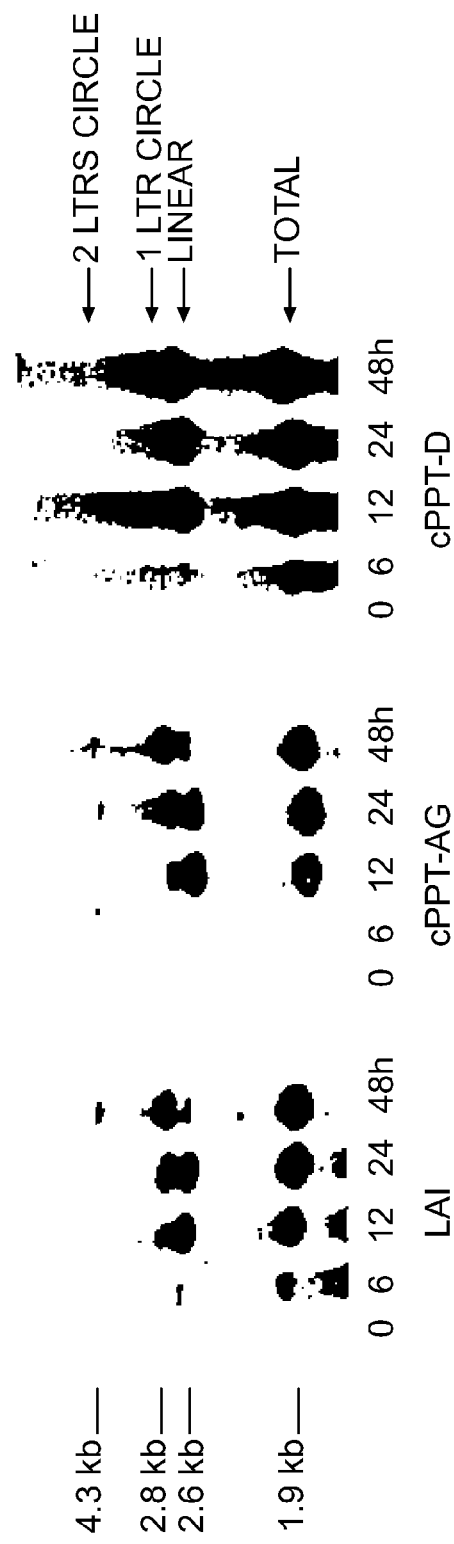
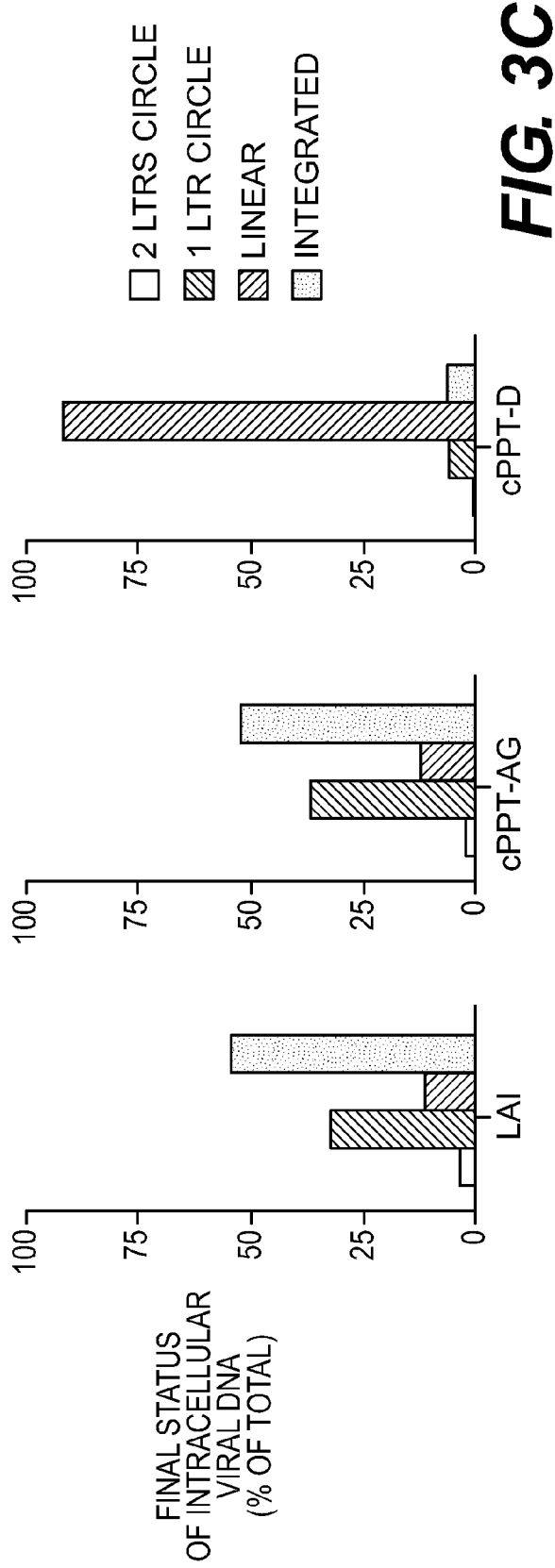

SEQUENCE LISTING

```
<160> NUMBER OF SEQ ID NOS: 24

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      MUTAGENESIS PRIMER BASED ON PLASMID pLAI3

<400> SEQUENCE: 1
caattttaaa agaagagggg ggatt                                         25

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:
      MUTAGENESIS PRIMER BASED ON PLASMID pLAI3

<400> SEQUENCE: 2
attcatccac aacttcaagc gccgcggtgg tattgggggg tac                     43

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:  PRIMER TO
      AMPLIFY NUCLEIC ACID ENCODING THE ENHANCED GREEN
      FLUORESCENT PROTEIN
```

<400> SEQUENCE: 3
ccggatcccc accggtcgcc acc                                    23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: PRIMER TO
      AMPLIFY NUCLEOTIDES ENCODING THE ENHANCED GREEN
      FLUORESCENT PROTEIN

<400> SEQUENCE: 4
ccctcgagct agagtcgcgg ccg                                    23

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: PRIMER TO
      AMPLIFY pUCLTRRI-.

<400> SEQUENCE: 5
cggaattcgg atccgcggcc gcatcgatct tgtcttcgtt gggagtg          47

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: PRIMER TO
      AMPLIFY pUCLTRRI-.

<400> SEQUENCE: 6
cggaattcag ccgtctcgag agatgctgca tataagcagc                  40

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: PRIMER TO
      AMPLIFY cPPT AND CTS OF pLAI3

<400> SEQUENCE: 7
gtggtcggcg ccgaattcac aaatggcagt attcatcc                    38

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: PRIMER TO
      AMPLIFY cPPT AND CTS OF pLAI3

<400> SEQUENCE: 8
gtcgtcggcg ccccaaagtg gatctctgct gtcc                        34

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: PRIMER TO
      AMPLIFY TRIPLEX SEQUENCE OF EF1 alpha PROMOTER ON THE MATRIX pLai

<400> SEQUENCE: 9
gtcgtcggcg ccgaattcac aaatggcagt attcatcc                                38

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: PRIMER TO
      AMPLIFY TRIPLEX SEQUENCE OF EF1 alpha PROMOTER ON
      THE MATRIX pLai

<400> SEQUENCE: 10
agcctcacga cgcgtatcag ccaaagtgga tctctgctg                               39

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: PRIMER TO
      AMPLIFY TRIPLEX SEQUENCE OF EF1 alpha PROMOTER ON
      THE MATRIX pEFpgkneo

<400> SEQUENCE: 11
ctgatacgcg tcgtgaggct ccggtg                                             26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: PRIMER TO
      AMPLIFY TRIPLEX SEQUENCE OF EF1 alpha PROMOTER ON
      THE MATRIX pEFpgkneo

<400> SEQUENCE: 12
cgggatcctg tgttctggcg gcaaac                                             26

<210> SEQ ID NO 13
<211> LENGTH: 23
<212> TYPE: DNA
<213> ORGANISM: Homo sapiens

<400> SEQUENCE: 13
ccctcgagct agagtcgcgg ccg                                                23

<210> SEQ ID NO 14
<211> LENGTH: 23
<212> TYPE: DNA
<213> ORGANISM: Homo sapiens

<400> SEQUENCE: 14
ccggatcccc accggtcgcc acc                                                23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: PRIMER FOR
      AMPLIFICATION OF pLAI3 VIRAL DNA

<400> SEQUENCE: 15

```
agaagaaatg atgacagcat g                                              21
```

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: PRIMER FOR
      AMPLIFICATION OF pLAI3 VIRAL DNA

<400> SEQUENCE: 16

```
tgccagttct agctctg                                                   17
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: PRIMER FOR
      SYNTHESIS OF PROBE FOR pTRIPGFP VECTOR

<400> SEQUENCE: 17

```
cagggacttg aaagcgaaag                                                20
```

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: PRIMER FOR
      SYNTHESIS OF PROBE FOR pTRIPGFP VECTOR

<400> SEQUENCE: 18

```
gcttgtgtaa ttgttaattt ctctgtc                                        27
```

<210> SEQ ID NO 19
<211> LENGTH: 7
<212> TYPE: PRT
<213> ORGANISM: Human immunodeficiency virus type 1
<220> FEATURE:
<221> NAME/KEY: PEPTIDE
<222> LOCATION: (1)..(7)
<223> OTHER INFORMATION: Partial HIV-1 cPPT sequence.

<400> SEQUENCE: 19

Asn Phe Lys Arg Lys Gly Gly
 1               5

<210> SEQ ID NO 20
<211> LENGTH: 19
<212> TYPE: DNA
<213> ORGANISM: Human immunodeficiency virus type 1

<400> SEQUENCE: 20

```
ttttaaaaga aaagggggg                                                 19
```

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: MUTATION
      INTRODUCED INTO THE HIV-1 cPPT SEQUENCE

<400> SEQUENCE: 21

```
ttttaaacgc aaaggtggt                                                 19
```

```
<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: MUTANT
      PEPTIDE OF HIV-1 cPPT SEQUENCE

<400> SEQUENCE: 22

Asn Phe Lys Arg Arg Gly Gly
 1               5

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: MUTATION
      INTRODUCED INTO THE HIV-1 cPPT CODING SEQUENCE

<400> SEQUENCE: 23
ttttaaaaga agagggggg                                               19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: MUTATIONS
      INTRODUCED INTO THE HIV-1 cPPT CODING SEQUENCE

<400> SEQUENCE: 24
cttcaagcgc cgcggtggt                                               19
```

LENTIVIRAL TRIPLEX DNA, AND VECTORS AND RECOMBINANT CELLS CONTAINING LENTIVIRAL TRIPLEX DNA

CROSS-REFERENCE TO RELATED APPLICATION

This application is a continuation of U.S. application Ser. No. 13/301,147, filed Nov. 21, 2011, which is a continuation of U.S. application Ser. No. 11/291,390, filed Dec. 1, 2005, now U.S. Pat. No. 8,093,042, which is a continuation of U.S. application Ser. No. 09/685,343, filed Oct. 11, 2000, now abandoned, which claims the benefit of U.S. Provisional Application Ser. No. 60/158,387, filed Oct. 12, 1999, all of which are hereby incorporated by reference.

BACKGROUND OF THE INVENTION

1. Field of the Invention

The present invention relates to the field of biotechnology, and especially to viral nucleic acids and cells containing viral nucleic acids. More particularly, the present invention relates to viral nucleic acid sequences that can be part of triplex DNA structures as well as nucleic acid vectors, viruses, and cells containing these viral nucleic acid sequences. It further relates to methods of using such DNA structures and nucleic acid sequences.

2. Description of Related Art

Gene transfer in hematopoietic stem cells (HSC) has great potential, both for gene therapy of inherited as well as acquired diseases, and for the understanding of mechanisms regulating normal and pathological hematopoiesis. As HSC have extensive proliferative capacities, stable gene transfer should include genomic integration of the transgene. Retroviruses based on Moloney murine leukemia virus (MoMLV) have been very popular because they integrate into the host cell genomes and can allow long-term transgene expression. However, these oncoretroviruses do not integrate in non-dividing cells, and most HSC are quiescent. Many pre-stimulation protocols using different cytokine associations have been developed to trigger cycling of HSC in order to render them transducible by oncovirus-derived, mitosis-dependant gene transfer vectors. However, cytokine stimulation induces differentiation together with proliferation and potentialities of HSC could be lost during the transduction process. This problem can be overcome by using lentivirus-derived vectors since lentiviruses have been shown to infect both dividing and non-dividing cells (Poznansky et al., 1991; Naldini et al., 1996). Initial reports published in the last three years using such lentivirus-derived vectors for transduction of HSC showed promising but very heterogenous results (Case et al., 1999; Evans et al., 1999; Uchida et al., 1998; Miyoshi et al., 1999).

Lentiviruses have evolved a nuclear import strategy which allows their DNA genome to cross the nuclear membrane of a host cell. This active nuclear import of lentiviruses accounts for their unique capacity, among retroviruses, to replicate efficiently in non-dividing target cells, such as tissue macrophages. The restriction of replication of oncoviruses like MoMLV to dividing cells appears to be due to the requirement for disruption of the nuclear membrane barrier during mitosis, allowing MoMLV pre-integration complexes (PICs) to enter the nucleus (Roe et al., 1993). Mitosis-independent replication of lentiviruses, at the origin of their in vivo replication strategy and hence of their pathogenicity, has also enabled the generation of lentiviral gene transfer vectors with promising therapeutic applications (Poznansky et al., 1991; Naldini et al., 1996).

The mitosis-independent replication of lentiviruses was first demonstrated by the productive infection of non-mitotic chondroid cells by the VISNA lentivirus (Thormar, 1963). Soon after its discovery, HIV was shown to replicate in differentiated primary macrophages (Gartner et al., 1986; Ho et al., 1986). HIV DNA integrates in the chromatin of non-mitotic target cells (Weinberg et al., 1991; Lewis et al., 1992), implying that HIV-1 PICs are able to cross the nuclear membrane of host cells (Bukrinsky et al., 1992). Thus, mitosis-independent nuclear import is a pivotal event responsible for the ability of lentiviruses to replicate in non-dividing cells.

The search for the viral determinants responsible for the active nuclear import of the HIV-1 DNA genome has constituted an active but controversial field of investigation. The presence of putative nuclear localization signals (NLSs) within the matrix (MA) and Vpr viral proteins has led to the proposition that they could act in a redundant manner in HIV-1 DNA nuclear import (Bukrinsky et al., 1993b; Emerman et al., 1994; Popov et al., 1998; von Schwedler et al., 1994). It has been proposed that phosphorylation of a small subset (1%) of MA molecules at a C-terminal tyrosine residue triggers their release from the plasma membrane and their association with HIV-1 integrase protein (Gallay et al., 1995a; 1995b). The contribution of these proteins to the karyophilic properties of HIV-1 PICs is currently a matter of strong debate (Freed and Martin, 1994; Freed et al., 1995; Fouchier et al., 1997; Freed et al., 1997; Koostra and Schuitemaker, 1999). More recently, NLS motifs have been identified in the integrase protein (IN) and mutations in these motifs have been reported to abolish the interaction of IN with karyopherin a, a cellular NLS receptor (Gallay et al., 1997).

SUMMARY OF THE INVENTION

Whatever the role of these candidate viral proteins in HIV nuclear import, the present invention shows that the retrotranscribed HIV-1 genome itself bears a cis-acting determinant for its nuclear import.

The invention provides a nucleic acid comprising a triple-stranded (triplex) structure, such as one from a lentivirus. The triplex stimulates entry of nucleic acids into the nucleus of cells. The nucleic acid can contain the cPPT and CTS cis-acting sequences of a lentivirus. The lentivirus can be any lentivirus, including, but not limited to, HIV-1, HIV-2, VISNA, EINV, FIV, and CAE. In embodiments, the nucleic acid is in the context of a vector, such as an expression vector.

Thus, the invention also provides a vector, for example, a nucleic acid vector. The nucleic acid vector can include sequences from any vector known to the skilled artisan as useful for transfer of nucleic acids into cells or for expression of nucleic acids in vivo or in vitro.

The invention further provides viruses and cells (eukaryotic and prokaryotic) containing the nucleic acid of the invention. The cells can be recombinant cells.

The invention additionally provides a method of transferring nucleic acid to a host cell nucleus by, for example, exposing the host cell to the nucleic acid, vector, virus, or cell of the invention, to provide a recombinant cell. The method of the invention permits high-efficiency transfer of nucleic acids to the host cell nucleus, such as the nucleus of a hematopoietic stem cell. High-efficiency transfer permits the skilled artisan to practice various methods of treatment, including, but not limited to, methods of prophylactic treatment, methods of ameliorative treatment, and methods of curative treatment.

For example, methods of gene therapy are enabled by this invention. In general, gene therapy can be used to treat blood diseases, brain diseases, viral disease, as well as many other inherited and acquired diseases.

Figure 1A:
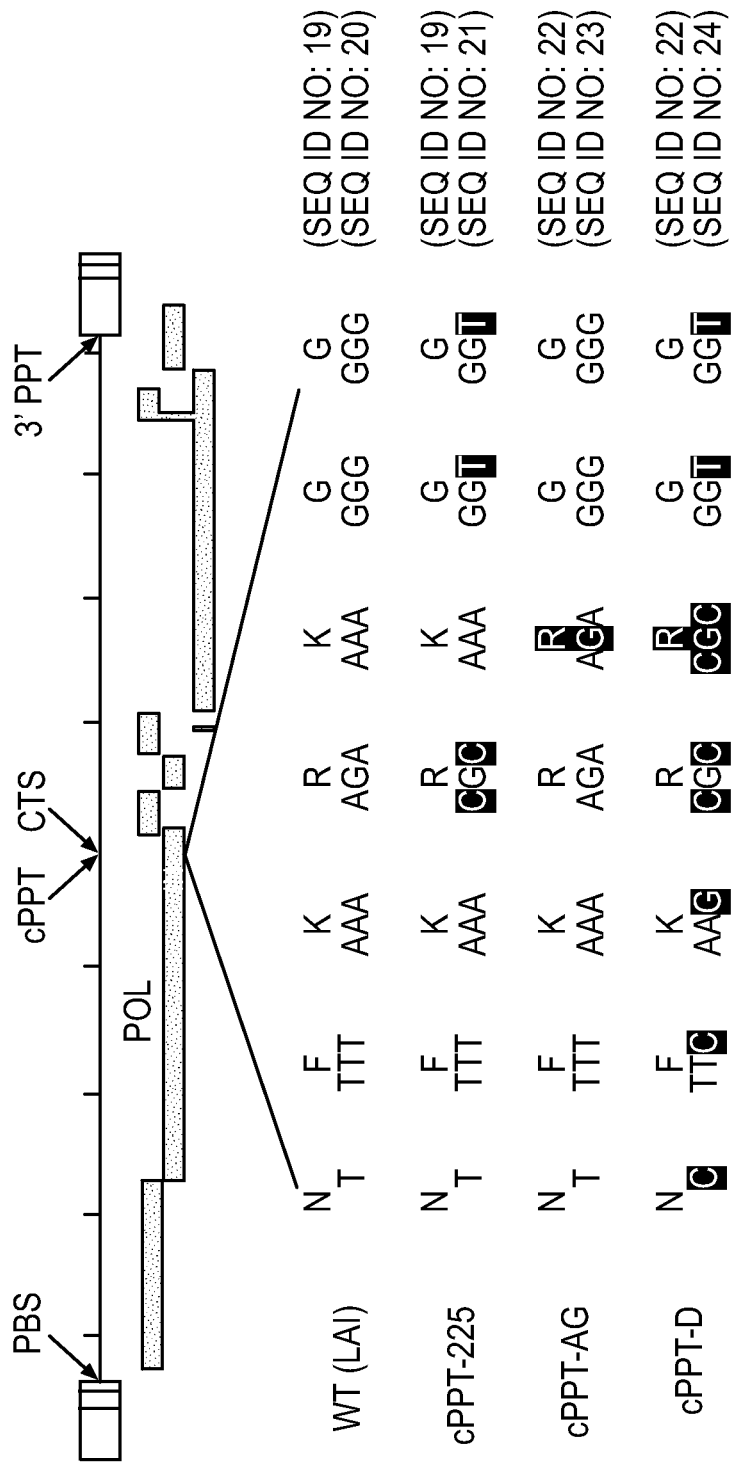
FIG. 1 shows that central initiation of reverse transcription is an important step in the replication cycle of HIV-1.

(A) Mutations introduced in the HIV-1 cPPT sequence. Conservative and semi-conservative cPPT mutant viruses were constructed. Semi-conservative mutant cPPT-D contains 10 mutations in the 19-mer cPPT. Mutant cPPT-AG is its control virus in which a single purine to purine mutation introduces the same amino acid change in the overlapping integrase coding region. Mutations are shown in reversed type.

(B) Impact of the mutations in the cPPT on HIV-1 infectivity. Virus replication kinetics on PHA stimulated PBLs (left panel) and MT4 cells (right panel). Cells were infected with equivalent amounts of viral particles according to the capsid antigen (p24) contents of viral supernatants. Virus production was followed over time by RT activity.

(C) Single cycle virus titrations in dividing or non-dividing aphidicolin-treated P4 cells (HeLa CD4-LTR LacZ). β-galactosidase activity was measured using a chemiluminescent assay. Results are expressed as relative light units (RLU)/sec/ng p24 of the inoculum, mean±SD of four independent experiments.

FIG. 2 depicts mutations in the cPPT that do not affect virus production, viral DNA synthesis nor the ability of viral DNA to integrate in vitro.

(A) Effect of mutations in the cPPT on virus production. HeLa cells were transiently transfected with pLAI, pcPPT-AG, or pcPPT-D plasmids. Virus production was measured by quantitation of p24 viral antigen in cell supernatants, 48 hours post-transfection.

(B) Effect of mutations in the cPPT on reverse transcription efficiency. P4 cells were infected with the same amounts of viral particles (300 ng of p24 antigen per $10^6$ cells) and DNA was extracted 12 hours later. Total amounts of reverse transcribed viral DNA, represented by an internal MscI HIV-1 fragment, was detected by Southern blot using the same DNA fragment as a probe and quantitated using a phosphorimager.

(C) Effect of mutations in the cPPT on in vitro integration. MT4 cells were co-cultivated with H9-LA1 or H9-cPPT-225 chronically infected cells. In vitro integration of viral pre-integration complexes, isolated from the cytoplasm of infected cells, was performed as previously described (Farnet and Haseltine, 1990). Each lane is loaded with cytoplasmic DNA from $2\times10^8$ infected cells.

FIG. 3 shows that central DNA triplex mutant viruses are defective in nuclear import of viral DNA.

(A) Strategy for the quantitative follow up of the synthesis, circularization, and integration of HIV-1 DNA. DNA from infected cells was extracted at various times post-infection, digested with MscI and XhoI, and analyzed by Southern blot using a probe overlapping the 5' MscI site. The internal 1.9 kb DNA fragment, common to all viral DNA species irrespective of their integrated or unintegrated state, indicates the total amount of viral DNA in infected cells. The 2.6 kb, 2.8 kb, and 3.4 kb signals corresponding, respectively, to unintegrated linear DNA, one, and two LTRs circular DNAs are revealed. Since the PCR generated probe exactly overlaps the MscI site, the intensity of each band is directly proportional to the amount of the corresponding viral DNA species. Thus, the amount of integrated proviral DNA can be calculated by subtracting from the total amount of viral DNA the signals of unintegrated linear and circular viral DNA.

(B) Southern blot analysis of viral DNA processing in infected cells. P4 cells were infected with equivalent amounts of each virus, normalized on the p24 contents of the supernatants. Infected cells were lysed at different times post-infection, DNA was extracted, and used for the quantitative analysis described above.

(C) Intracellular viral DNA profiles, on completion of one cycle of infection (48 hours post-infection). Results are expressed as percentages of total viral DNA. Similar intracellular viral DNA profiles were obtained using MT4 cells (data not shown).

Figure 4A:
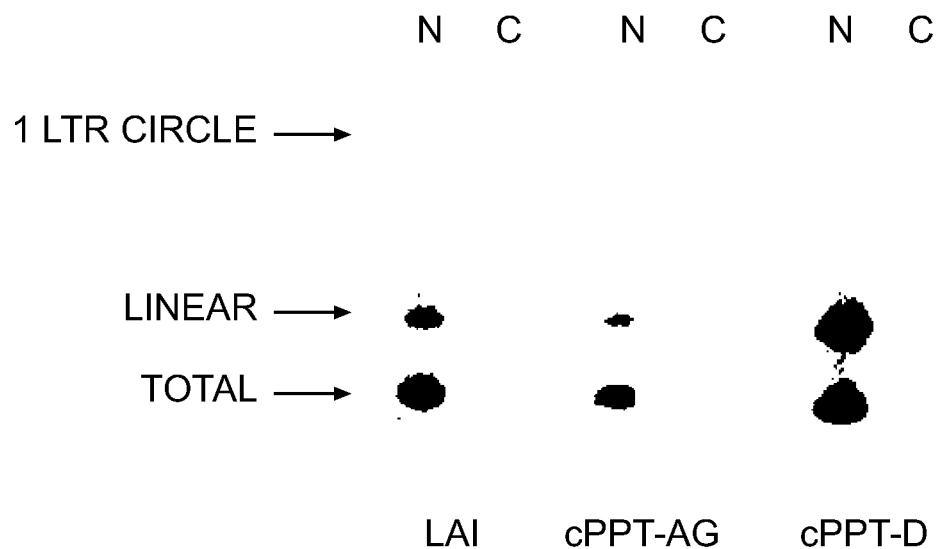

FIG. 4 shows that linear DNA from central DNA triplex mutant viruses accumulates at the vicinity of the nuclear membrane.

(A) Nucleus/cytoplasm fractionation of infected P4 cells. Southern blot analysis of viral DNA from nuclear (N) and cytoplasmic (C) fractions, 24 hours post infection. Fractionation based on triton lysis was performed as previously described (Belgrader et al., 1991). DNA was restricted with MscI and hybridized using the MscI site overlapping probe.

(B) Detection of individual HIV-1 genomes by Fluorescence In Situ Hybridization (FISH). P4 cells were infected at high multiplicity (2 μg of p24 antigen per $10^6$ cells), and hybridized using a full length HIV-1 genome probe. Fluorescent signals were amplified by tyramid precipitation. Optical sections through cells were analyzed by deconvolution microscopy.

FIG. 5 shows that the insertion of the central DNA triplex in an HIV-1 based vector enhances GFP transduction and nuclear import of the vector DNA genome.

(A) Schematic diagram of the vector genomes. cPPT and CTS central cis active sequences of the HIV-1 genome, responsible for the formation of the DNA triplex during reverse transcription, were inserted in a central position in the previously described HR GFP vector (Naldini et al., 1996). TRIPinv-GFP includes the central DNA triplex sequence in the reverse, non-functional orientation.

(B) Comparative efficiency of GFP transduction using HIV vectors with or without a central DNA triplex. Dividing or non dividing (aphidicolin treated) HeLa cells were used as targets. GFP fluorescence was quantitated 48 hours post-transduction using a microplate fluorometer (Wallac). Results are expressed as the mean±SD of a representative experiment performed in triplicate. Pseudotransduction of GFP activity was subtracted from the signal.

(C) Southern blot analysis of vector DNA processing in transduced cells. Transduced HeLa cells were lysed at different times post-infection, DNA was extracted, restricted, and Southern blotted using a similar strategy as for the viruses. MscI digestion is replaced by EcoNI and AvaII, and the probe is a PCR DNA fragment overlapping exactly the EcoNI site.

(D) Quantitative analysis of vector DNA intracellular status, 48 hours post infection. Results are presented as percentages of total vector DNA.

FIG. 6 depicts a model for DNA triplex dependent HIV-1 genome nuclear import.

(A) Overview of the observed phenotype of central DNA triplex mutant viruses. Central initiation and termination steps of HIV-1 reverse transcription creates a long plus strand DNA flap structure: the central DNA triplex. HIV-1 plus strand is synthesized as two discrete half-genomic segments. A downstream segment is initiated at a central copy of the polypurine tract sequence (cPPT). The upstream segment terminates downstream the cPPT, after a 99 nucleotide long strand displacement event, blocked by the central termination sequence (CTS). At completion of a single cycle of infection, viral DNA from wild-type virus is almost fully processed into integrated provirus (≈55%), 1LTR (≈35%), and 2LTRs circular DNA (<5%), while a small fraction remains as linear DNA (<10%). Mutations in the cPPT affects the formation of the central DNA triplex. The final reverse transcription product of a central initiation mutant virus is a continuous double-stranded linear DNA lacking the central DNA triplex (Charneau et al., 1992). Viral DNA from cPPT-D mutant virus accumulates in infected cells as linear DNA molecules, and localizes at the vicinity of the nuclear membrane.

(B) Two speculative mechanisms for triplex dependent HIV-1 genome nuclear import via maturation of the reverse transcription complex (RTC) into a pre-integration complex (PIC) and linear DNA translocation through the nuclear pore. HIV-1 reverse transcription probably occurs within a structured (ordered) complex surrounded by an assembly of capsid proteins. The size of RTC exceeds the exclusion diameter of the nuclear pore. Before translocation, RTC undergoes a maturation into a smaller PIC with loss of the capsid proteins (Karageorgos et al., 1993). Formation of the DNA triplex signals the end of the viral DNA synthesis and could signal the escape of the HIV DNA from the capsid assembly. In the PIC, the extremities of the linear DNA are probably bridged together after dimerization of integrase proteins bound to the tips of the LTRs (Miller et al., 1997). The DNA triplex being at a central position, one logical structure for HIV-1 PIC would be a double filament, symmetrically folded on either side of the central triplex by the integrase dimerization. The DNA triplex would then constitute an apex which could interact with karyophilic shuttling proteins, allowing the passage of the HIV-1 DNA filament through the nuclear pore. In cPPT mutant viruses, a default of RTC maturation into PIC would induce an accumulation of integral viral capsids at the nuclear pore. Alternatively, the absence of the DNA triplex in cPPT mutant linear DNA would prohibit the interaction with shuttling proteins forbidding translocation of HIV-1 genome through the nuclear pore. In both cases, DNA from cPPT mutant viruses accumulates as linear DNA at the vicinity of the nuclear membrane.

FIG. 7 shows the results of transduction experiments using CD34+ human cord blood cells.

(A) FACS analysis of human cord blood CD34+ cells transduced for 24 hours in the presence of 100 ng/ml of viral P24 in conditions described herein. Analysis was performed 48 hours after washing of the cells at the end of the 24 hour transduction period. Percentages are expressed as proportions of morphologically gated hematopoietic cells. X mean indicates the mean value of green fluorescence intensity.

(B) GFP expression was analyzed at day 5 post transduction.

Figure 8A:
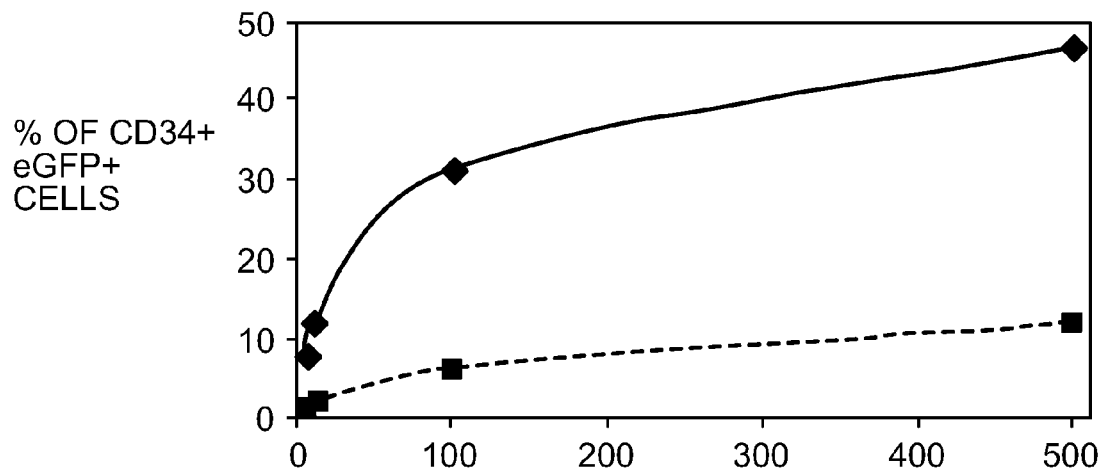
Figure 8B:
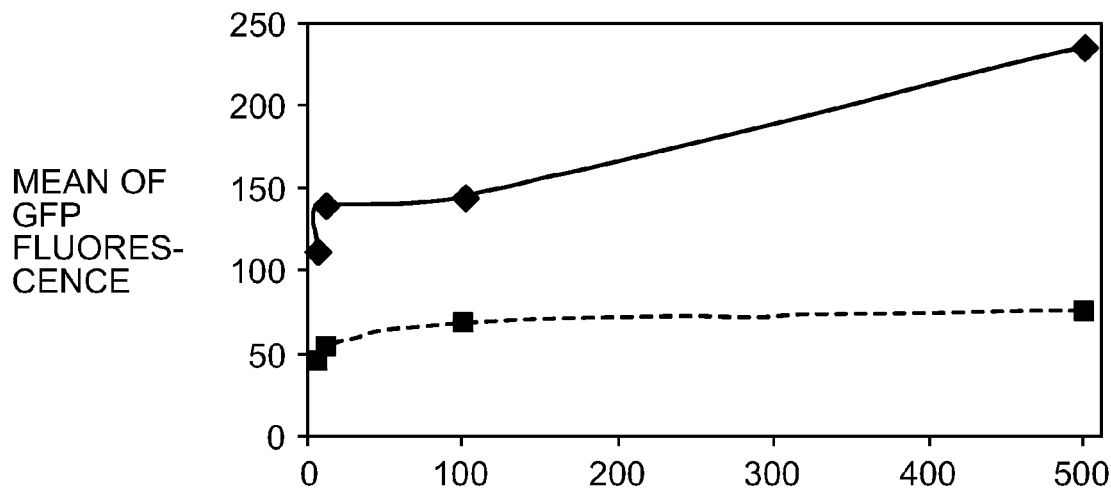
Figure 8C:
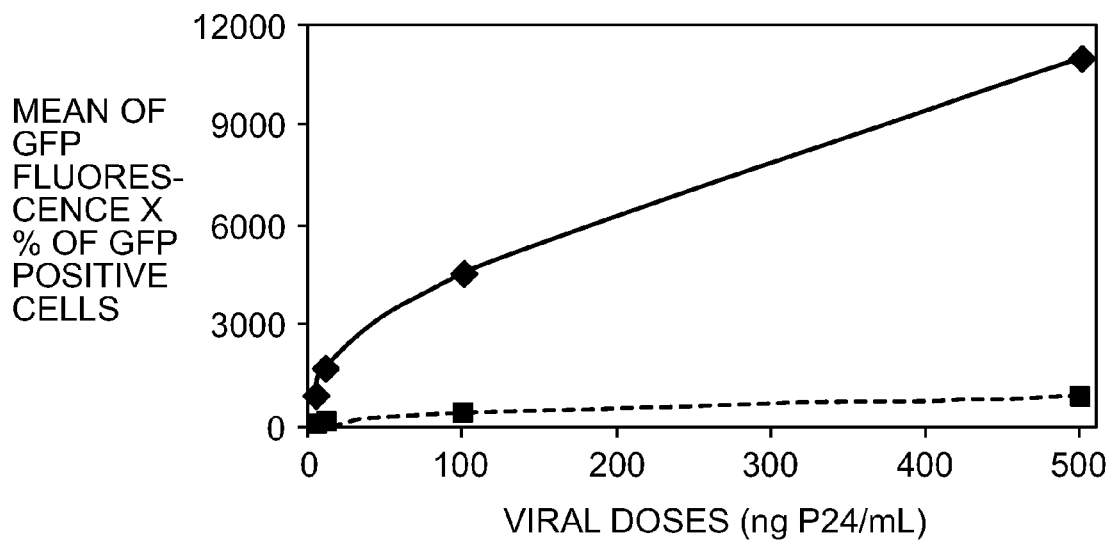

FIG. 8 diagrammatically represents the effect of viral dosage on transfection efficiency.

(A) The percentage of CD34+ cells expressing eGFP.

(B) The mean value of GFP fluorescence intensity of CD34+ eGFP+ cells.

(C) The mean value of GFP fluorescence intensity of CD34+ eGFP+ cells multiplied by the percentage of CD34+ eGFP+ cells. CD34+ cells were transduced for 24 hours under the conditions specified herein with the lentiviral vector including the eGFP coding sequence under the control of the CMV promoter, and including (thick line) or without (dashed line) the triplex structure. Analysis was performed 48 hours after washing of the cells at the end of the 24 hour transduction period.

FIG. 9 depicts FACS analysis of human cord blood CD34+ cells transduced for 24 hours under the conditions described in the text with a lentiviral vector having an intact HIV-1 LTR (left panels) or a U3 deleted HIV-1 LTR (right panels) and an internal CMV promoter (upper panels) or the EF-1 alpha promoter (lower panels).

(A) Analysis was performed 48 hours after washing of the cells at the end of the 24 hour transduction period.

(B) Analysis was performed 120 hours after washing of the cells at the end of the 24 hour transduction period. The analysis distinguishes between bright (immature) and dull CD34 cells.

Percentages are expressed as proportions of morphologically gated hematopoietic cells. The second number, when indicated, represents the mean of green fluorescence.

DETAILED DESCRIPTION OF THE INVENTION

Figure 6A:
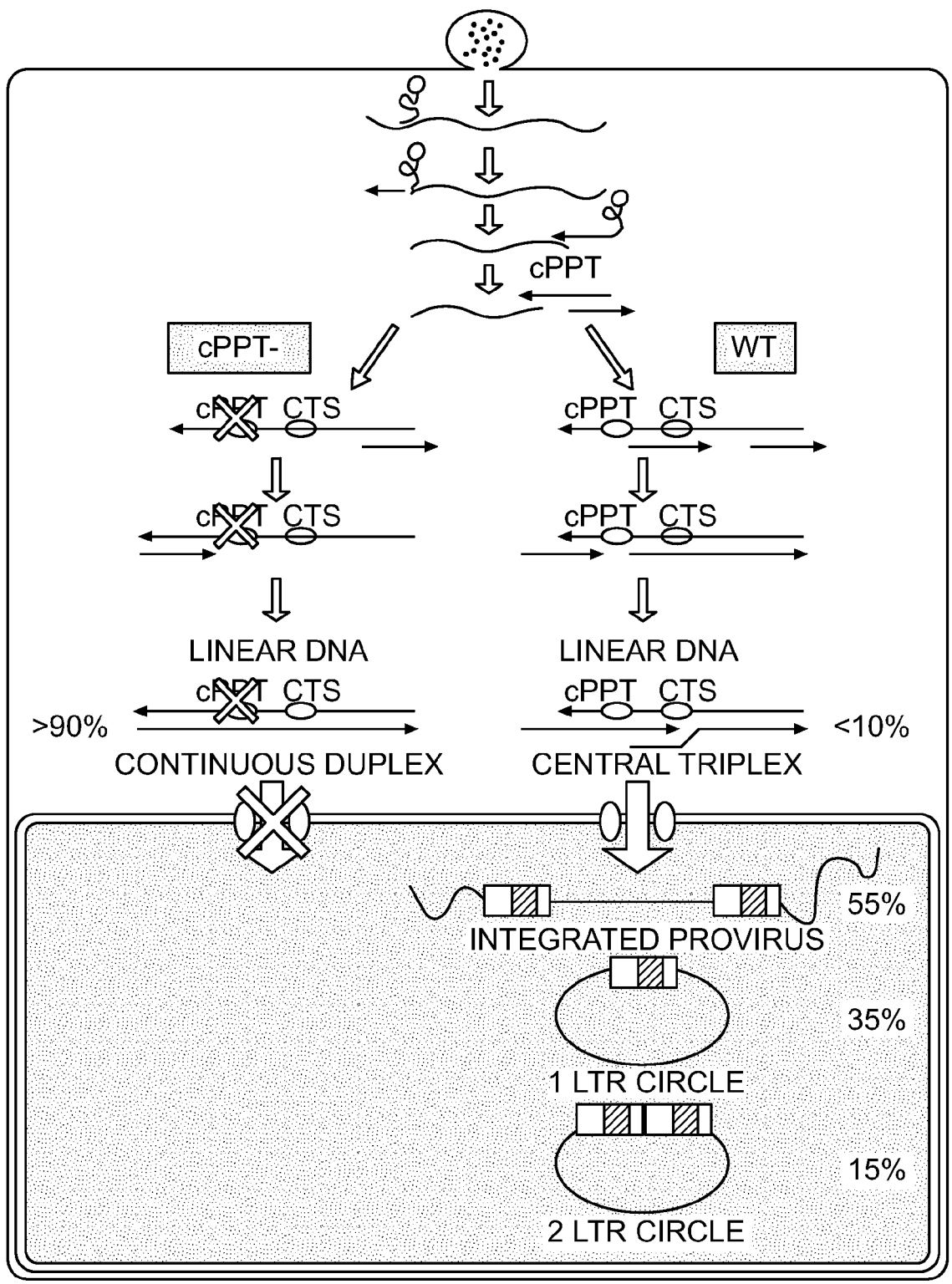

We have previously shown that HIV-1 has evolved a complex reverse transcription strategy, which differs from that of oncoviruses by two steps occurring at the center of the genome: one additional initiation of plus strand synthesis coupled with a termination step. HIV-1 plus strand DNA is synthesized as two discrete half-genomic segments. An additional copy of the polypurine tract cis-active sequence, present at the center of all lentiviral genomes (cPPT), initiates synthesis of a downstream plus strand (Charneau et al., 1991, 1992). The upstream plus strand segment initiated at the 3' PPT will, after a strand transfer, proceed to the center of the genome and terminate after a discrete strand displacement event (FIG. 6A). This last chronological event of HIV-1 reverse transcription is controlled by the central termination sequence (CTS) cis-active sequence, which ejects HIV-1 reverse transcriptase (RT) at this site in the specific context of strand displacement synthesis (Charneau et al., 1994; Lavigne et al., 1997). Thus, the final product of HIV-1 reverse transcription is a linear DNA molecule bearing in its center a stable 99 nucleotide long DNA flap, here referred to as the central DNA triplex (FIG. 6A).

Central initiation and termination mutant viruses both synthesize a reverse transcription product devoid of a wild type DNA triplex. As depicted in FIG. 6A, in the case of a central initiation mutant, the final product is a continuous double-stranded linear DNA lacking the central triplex (Charneau et al., 1992). The downstream plus strand segment initiated at the cPPT is not synthesized. Thus, no strand displacement occurs at the center of the genome; elongation of the transferred plus strand proceeds all along the genome. In the case of a central termination mutant, central strand displacement events are no longer controlled by the mutated CTS sequence and longer, randomly distributed plus strand overlaps are generated, as compared to the discrete wild type DNA triplex (Charneau et al., 1994). Mutations in the cPPT or CTS cis-active sequences severely impair HIV replication, suggesting a direct role of the central triplex in the retroviral life cycle (Charneau et al., 1992; Hungnes et al., 1992; Charneau et al., 1994).

The present invention discloses that the central DNA triplex of HIV-1 is involved in a late step of HIV-1 genome nuclear import, immediately prior to, or during, viral DNA translocation through the nuclear pore. Hence the distinctive features of lentiviral reverse transcription account, at least in part, for the unique capacity of lentiviruses, among retroviruses, to replicate in non-dividing cells. The invention also discloses that HIV gene transfer vectors lacking the central DNA triplex exhibit a strong nuclear import defect. This invention establishes that the insertion of the central cis-active sequences of the HIV-1 genome into a previously described HIV vector (Naldini et al., 1996) increases the transduction efficiency by complementing the nuclear import defect of the original vector DNA to wild type levels. This finding provides additional and independent evidence for the role of the central DNA triplex in HIV-1 nuclear import.

The description of the DNA triplex as a nuclear import determinant of lentiviruses has important implications for the design of efficient lentiviral vectors. Since the infection of non-dividing target cells by lentiviruses relies on their use of an active nuclear import pathway, it is preferable to maintain the lentiviral nuclear import determinants in derived vector constructs. Classical retroviral vector constructs are replacement vectors in which the entire viral coding sequences between the LTRs are deleted and replaced by the sequences of interest (Miller A D, 1997). In the case of lentiviral vectors, this classical strategy leads to the deletion of the central cis-active sequences cPPT and CTS. The important role of the triplex in HIV nuclear import implies that such replacement vector constructs are not optimal. This finding establishes the fact that the DNA triplex nuclear import determinant is operative in the heterologous context of an HIV-1 derived lentiviral vector. The DNA triplex per se out of the context of the native HIV-1 genome can promote nuclear import of heterologous DNA sequences (PCT France No. 98 05197, 24 Apr. 1998). The presence of the DNA triplex sequence induces a marked increase of gene transduction efficiency in hematopoietic stem cells.

Thus, in one aspect, the present invention provides nucleic acids (DNA or RNA, or analogs thereof) that are capable of participating in triplex nucleic acid structures (i.e., triple-stranded nucleic acids). In embodiments of the invention, the nucleic acids are lentiviral sequences. In embodiments, the nucleic acids are derived from lentiviral sequences, such as by directed mutagenesis (i.e., intentional deletion, insertion, or replacement of at least one nucleotide) or selective pressure mutagenesis. The nucleic acids of the invention permit high-efficiency transfer of nucleic acids into host cells, and especially into host cell nuclei. Because of this ability, genes that are operably or physically linked to the nucleic acids of the invention can be expressed at high levels and/or in a high percentage of cells exposed to the nucleic acids. DNA inserted in a triple-stranded region of a lentiviral genome in accordance with the present invention is particularly stable in the construct, and aids in achieving a high level of transduction and transfection.

In a preferred embodiment, the invention provides a three-stranded DNA sequence induced by the cPPT and CTS regions of a lentivirus, which is capable of inducing a high rate of entry of vector DNA into a host cell nucleus, or capable of increasing the rate of nuclear import of vector DNA. In embodiments, the three-stranded DNA sequence can be covalently linked to a heterologous nucleic acid sequence, such as a reporter gene or gene of other interest. For example, the nucleic acid of the invention can comprise a heterologous nucleic acid sequence that encodes a peptide, polypeptide, or protein. In embodiments, the heterologous nucleic acid sequence is present within the triple-helix region. In embodiments, the heterologous nucleic acid sequence is present on the same nucleic acid as the triple-helix region, but outside of the triple helix. In embodiments, a single nucleic acid comprises more than one three-stranded sequence induced by the cPPT and CTS regions of a lentivirus.

In another aspect, the present invention provides vectors, such as shuttle vectors, expression vectors, integration vectors, transposons, retrotransposons, and the like, which contain at least one sequence capable of participating in the formation of triplex nucleic acid structures. In embodiments, the vector comprises a single sequence capable of participating in the formation of triplex nucleic acid structures. In embodiments, the vector comprises more than one sequence capable of participating in the formation of triplex nucleic acid structures. The vectors can be used to transfer the nucleic acids of the invention from one cell to another, to aid in generation of large quantities of the nucleic acids of the invention, and to serve as a base molecule into which other nucleic acid sequences of interest (e.g., reporter genes, therapeutic genes) can be inserted.

In yet another aspect, the present invention provides a method for efficiently infecting, transfecting, or transducing cells with a viral nucleic acid sequence comprising at least one sequence that can participate in triplex nucleic acid structures. In embodiments, the method comprises exposing a cell, or a plurality of cells, to at least one copy of a nucleic acid, vector, virus, or cell of the invention. In embodiments, the step of exposing the cell or cells to the nucleic acid, vector, virus, or cell of the invention is conducted under conditions such that the nucleic acid, vector, virus, or cell of the invention can enter the target (host) cell or cells. In preferred embodiments, the conditions are such that high levels of the nucleic acid, vector, virus, or cell of the invention enter the target cell or cells.

In embodiments, the method is highly efficient, permitting insertion of the nucleic acid of the invention into the nucleus of 30% or greater of the cells exposed to the nucleic acid. In embodiments, the percentage of nuclei taking up the nucleic acid of the invention is 40% or greater, for example 50% or greater, 60% or greater, 70% or greater, 80% or greater, or 90%-100%. In preferred embodiments, the percentage of nuclei taking up the nucleic acid of the invention is greater than 80%, more preferably, greater than 85%, and most preferably, greater than 90%, such as greater than 95%. In embodiments, the cells are infected or transfected with whole viruses (including phages) or bacteria containing the nucleic acids of the invention. In embodiments, the nucleic acids of the invention are introduced into the cells using mechanical and/or chemical means (e.g., electroporation, liposome fusion). In embodiments, naked nucleic acid according to the invention is taken up by target host cells.

Thus, in an embodiment, the invention provides the use of a nucleotide sequence comprising the cPPT and CTS regions, which adopts a three-stranded DNA structure (triplex) after reverse transcription, in a lentiviral or retrotransposon vector and which stimulates entry of, and the rate of nuclear import of, the vector DNA into the nucleus of a transduced cell.

In an aspect of the invention, recombinant cells are provided that contain the nucleic acids or vectors of the invention. The recombinant cells can be any cell (prokaryotic or eukaryotic), including a progeny or derivative thereof. Thus, the invention includes cells that are created using a cell of the invention. In embodiments, the cells are eukaryotic. In embodiments, the cells are mammalian cells, such as HeLa cells or hematopoietic cells, such as hematopoietic stem cells. Thus, in embodiments, the invention provides a process of transducing eukaryotic cells, wherein the process comprises use of a three-stranded DNA sequence induced by the cPPT and CTS regions of a lentivirus, which is capable of inducing a high rate of entry of vector DNA into a host cell nucleus, or capable of increasing the rate of nuclear import of vector DNA.

Because the recombinant cells of the invention can express a heterologous gene of interest at high levels, these cells can be used in numerous applications. Applications include, but are not limited to, production of high levels of proteins of interest (such as proteins of therapeutic value) in cell culture and production of a protein of interest in vivo by introduction of the recombinant cell of the invention into an individual in need of the protein. The individual can be an animal or a human. Accordingly, the invention has both veterinarian applications as well as medical ones.

In embodiments, this aspect of the invention provides a method of producing a recombinant protein of interest by exposing a target cell to a nucleic acid, vector, or virus of the invention and permitting the target cell to take up nucleic acid of the invention, for example, through transduction, transformation, or transfection. Following introduction of the nucleic acid into the target cell, the cell is cultured under conditions whereby the recombinant protein of interest is expressed, and thus produced by the target cell, which now is considered a recombinant cell according to the invention. Although the method can be practiced on a single, individual cell, it is evident that the method will often be more practical if practiced on a collection of cells in which all of the cells are clones. As used herein, "cell" refers to an individual cell or a collection of identical cells.

The method can further include purifying or isolating the protein of interest from the recombinant cell or cell culture fluid. In such a method, protein expression and purification procedures known to those of skill in the art can be applied. These procedures are well known to those of skill in the art and therefore need not be detailed here.

In a preferred embodiment, this aspect of the invention provides a process for expressing a gene of interest in vitro, wherein the process comprises: a) exposing target cells to an isolated or purified nucleic acid comprising a gene of interest and at least one copy of the cPPT and CTS cis-acting regions of a retrovirus, wherein the cPPT and CTS regions induce a three-stranded DNA structure, under conditions that permit uptake of the nucleic acid into the target cell to create a recombinant cell, and b) culturing the recombinant cell under conditions that permit at least part of the nucleic acid to be transferred to the nucleus of the recombinant cell and the gene of interest to be expressed. In embodiments, the process uses a vector according to the invention.

Thus, the invention provides a method of expressing a gene of interest in vitro, for example, in tissue culture. In embodiments, the method comprises exposing target cells to a nucleic acid, vector, virus, or cell of the invention under conditions where the target cell can take up the molecule of the invention containing the gene of interest. The recombinant cell thus made is then allowed to grow and replicate under conditions where the gene of interest is expressed. In embodiments, the in vitro method of gene expression is coupled to a method of purifying or isolating the protein of interest. In these embodiments, the protein of interest can be purified or isolated from other cellular components using techniques known to those of skill in the art, including, but not limited to, liquid chromatography, precipitation, centrifugation, gel filtration, and affinity chromatography. Suitable techniques are known to those of skill in the art and need not be detailed here.

Thus, the invention also provides a method of expressing a gene of interest in vivo, for example, in an individual in need of the protein expressed by the gene. In embodiments, the method of expressing a gene in vivo comprises making a recombinant cell outside the individual by exposing a host cell to a nucleic acid, vector, virus, or cell of the invention, to make a recombinant cell according to the invention. The recombinant cell of the invention is then administered to, introduced into, or otherwise exposed to, the individual, whereupon the gene of interest is expressed. For example, the method can comprise administering a recombinant cell comprising a nucleic acid of the invention to an individual, and permitting the recombinant cell to express the nucleic acid within the individual's body. In preferred embodiments, the recombinant cell is a hematopoeitic stem cell. In embodiments, the recombinant cells are first purified or isolated from non-recombinant cells, then administered to, introduced into, or otherwise exposed to, the individual.

In other embodiments, the method of expressing a gene in vivo comprises exposing (e.g., administering, introducing, etc.) the individual to a nucleic acid, vector, and/or virus of the invention. In embodiments, the nucleic acid, vector, and/or virus transfects/transduces/infects at least one of the individual's cells, whereupon the gene of interest is expressed. For example, the method can comprise administering a nucleic acid, vector, or virus of the invention to an individual in an amount and form sufficient to result in expression of the gene of interest within the individual's body. Preferably, the method results in expression of the gene of interest in a target tissue or cell.

In an embodiment, this aspect of the invention provides a process for treating an individual suffering from, or having a high likelihood of developing, a disease or disorder having a genetic basis. The process comprises administering a retroviral vector comprising a) a nucleic acid encoding a therapeutic protein and b) at least one copy of the cPPT and CTS cis-acting regions of a retrovirus, wherein the cPPT and CTS regions induce a three-stranded DNA structure, to the individual in an amount sufficient to result in expression of the therapeutic protein in an amount sufficient to treat the disease or disorder. The treatment can be prophylactic, ameliorative, or curative. The process can treat a blood disease or disorder, a brain or nervous system disease or disorder, or a developmental disease or disorder. Techniques for introducing and/or expressing genes in vivo are known to those of skill in the art. The practitioner may select the technique most suitable for the given protein or target tissue or cell.

Accordingly, the invention provides a process of treating a host comprising use of a retroviral vector containing a three-stranded DNA sequence induced by the cPPT and CTS regions of a lentivirus, which is capable of inducing a high rate of entry of vector DNA into a host cell nucleus, or capable of increasing the rate of nuclear import of vector DNA.

In accordance with the above aspects of the invention, a kit is also provided. The kit can contain at least one nucleic acid, at least one vector, at least one virus, or at least one cell of the invention, or a combination of any or all of those. The kit can provide each of the above embodiments of the invention together in a single composition or separately, as for example, in different containers. In embodiments, the kit includes some or all of the reagents and supplies necessary to use the nucleic acids, vectors, viruses, and cells of the invention for the desired purpose.

The present invention discloses an original mechanism of HIV-1 nuclear import with a crucial role of a three stranded DNA structure, the DNA triplex, in this mechanism. HIV-1 has evolved a complex reverse transcription strategy, whereby a central strand displacement event, consecutive to the central initiation and termination of reverse transcription, creates a DNA triplex at the center of unintegrated linear HIV-1 DNA molecules. This DNA triplex acts in turn as a cis-active determinant of the nuclear import of the HIV-1 genome. The invention shows that central initiation and termination, two distinctive steps of HIV-1 reverse transcription, account for the capacity of HIV-1 to infect non-dividing target cells.

The Examples of the invention further show that lack of the DNA triplex leads to a virus which is almost non-infectious in dividing or non-dividing cells. Although mutations in cPPT do not affect the rate of synthesis of viral DNA or its ability to integrate in vitro, most of the retrotranscribed DNA molecules from the cPPT mutant virus accumulate over time as unintegrated linear DNA. In contrast, linear DNA from the wild-type virus is almost fully processed into integrated proviruses and DNA circles. The intracellular DNA profile of cPPT mutant viruses points to a defect of nuclear import, the viral DNA accumulating as linear molecules as a consequence of its lack of access to the nuclear compartment where it could integrate or circularize. A late defect of viral DNA import, most probably affecting translocation through the NPC, is demonstrated by fractionation of infected cells and direct visualization (FISH) of intracellular viral DNA. The triplex defective linear DNA molecules associate with the nuclear membrane.

The invention focuses on the analysis of cPPT mutant viruses, which are characterized by the absence of a central DNA triplex. Most of the experiments presented herein were also conducted with previously described CTS mutant virus (Charneau et al., 1994), with the same results (data not shown). In the CTS mutant virus, reverse transcription produces linear DNA molecules containing larger, randomly distributed plus strand overlaps, as compared to the discrete central DNA triplex of the wild-type virus. Thus, not only the presence of the DNA triplex, but also its structural integrity, is important for the nuclear import of HIV DNA.

The invention shows that the DNA triplex is operative in the context of an HIV-1 based vector system. Its insertion into a vector devoid of the triplex reverts a strong defect of nuclear import of the vector DNA to wild-type levels of nuclear import.

The central DNA triplex is a common nuclear import determinant of lentiviruses. The location of the central DNA triplex has been precisely defined in the case of HIV-1. Central strand displacement starts at the first nucleotide following the cPPT sequence (Charneau and Clavel, 1991) and stops in general 99 nucleotides downstream, at the ter2 site of the CTS sequence (Charneau et al., 1994). The three dimensional configuration of the three DNA strands of the triplex is as yet unknown. Nevertheless, the presence of a DNA triplex at the center of the genome can be generalized to all lentiviruses. A central copy of PPT is a common feature of all lentiviral genomes and a putative CTS terminator element, revealed by the presence of $(A)_n$ and $(T)_n$ tracts, also exists approximately 100 nucleotides downstream (Charneau et al., 1994). The central DNA triplex of the ungulate lentivirus EIAV has been characterized recently (Stetor et al., 1999). A central strand discontinuity in VISNA virus DNA, referred to as a gap, but most probably a nick resulting from the central strand displacement, was revealed by S1 nuclease cleavage (Harris et al., 1981). Since mitosis-independent replication has been described for most lentiviruses (Gartner et al., 1986; Thormar, 1963), the role of the DNA triplex in nuclear import described here for HIV-1 can be generalized to all lentiviruses.

Without being limiting, the invention provides a mechanistic hypothesis for the role of the central DNA triplex in HIV-1 nuclear import as follows: A three stranded DNA structure acting as a cis-determinant of its nuclear import is a novel biological phenomenon with no known cellular or viral counterparts. Any hypothesis of a molecular mechanism describing the role of the central DNA triplex in HIV nuclear import is therefore speculative. The central triplex could act as a viral determinant for initiation of the uptake of the HIV DNA filament through the nuclear pore. This could be achieved through direct interaction of the DNA triplex with components of the pore, or alternatively through interaction of the triplex with cellular or viral proteins which shuttle between the cytoplasm and the nucleus of the host cell and could drag the HIV genome into the nucleus. Translocation of the 9.7 kb HIV genome through a nuclear pore of maximum diameter of 26 nm must occur in a specific orientation, after recognition of one extremity of the HIV-1 DNA filament to initiate the uptake. A similar situation arises in the nuclear export of messenger RNA, where uptake of the RNA filament through the pore is guided by the 5' Cap structure (Hamm and Mattaj, 1990).

Figure 6B:
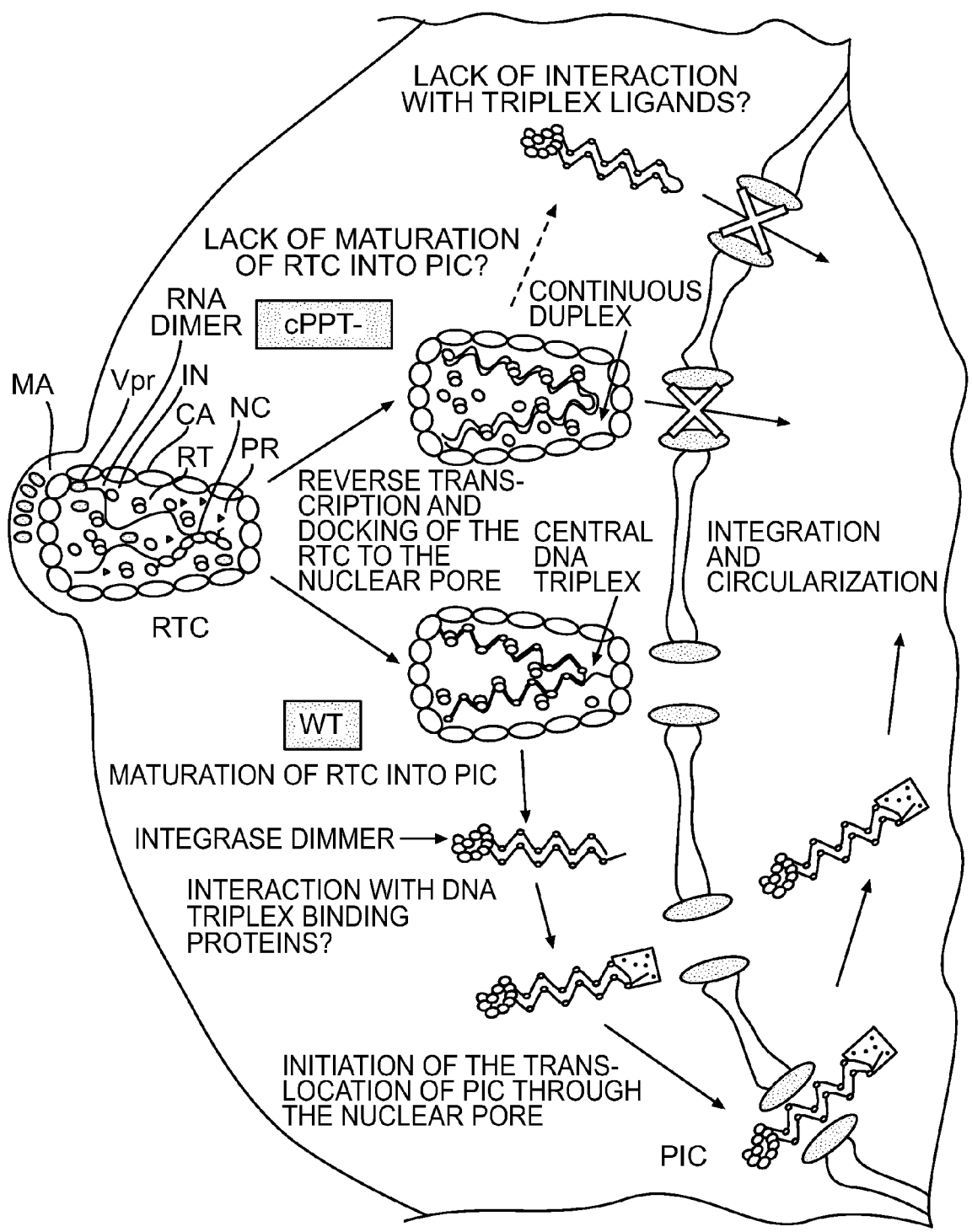

Although the conformation of HIV-1 PICs is not well known, it has been established that the extremities of the linear DNA are bridged together, probably after dimerization of the integrase proteins bound at the tips of the LTRs (Miller et al., 1997). Interestingly, the cPPT and CTS cis-active sequences are found at a central position in all lentiviral genomes. One logical structure for lentiviral PICs would be a double DNA filament, symmetrically folded on either side of the central triplex by the integrase dimerization (FIG. 6B). The triplex would then constitute one apex of a filamentous HIV-1 PIC and the integrase dimer the opposite apex. In cPPT mutant PICs, the absence of a DNA triplex would lead to their lack of recognition by the nuclear pore machinery or the shuttling proteins. Identification of the protein ligands of the central DNA triplex promises to be of primary importance both for our understanding of HIV-1 PIC nuclear import and for the eventual development of drugs targeting this step of HIV replication.

Another mechanistic hypothesis to explain the properties of triplex mutant viruses would involve a defect in the maturation of HIV capsids into PICs, prior the translocation of viral DNA into the nucleus. According to this model, triplex defective viral DNA would remain trapped as integral viral capsids, unable to translocate. Retroviral reverse transcription does not take place at high dilution of the viral components in the cytoplasm of infected cells, but requires the structural environment of a reverse transcription complex where components are confined in a capsid protein assembly. The HIV capsid size exceeds the maximum exclusion diameter of a nuclear pore (Dworetzky et al., 1998; Gelderblom, 1991). Therefore, before viral DNA can enter the nucleus, the HIV reverse transcription complexes must undergo maturation into PICs of size compatible with translocation through the nuclear pores (Karageorgos et al., 1993). The maturation of viral capsids prior to nuclear translocation is well established in several other viral systems in which the replicative cycle involves translocation of the DNA genome through the nuclear membrane of the host cell (Whittaker and Helenius, 1998). Whereas reverse transcription within viral capsids has been physically demonstrated for MLV (Bowerman et al., 1989), this has not yet been possible for HIV-1 possibly due to the fragility of HIV-1 capsids (Borroto-Esoda and Boone, 1991). The HIV reverse transcription complex contains numerous copies of RT polymerase (about 30 to 50 per capsid) (Panet et al., 1975). Owing to the important distribution of HIV-1 reverse transcriptase, a high stoichiometry of enzyme to viral RNA template is necessary to overcome a number of limiting steps of reverse transcription such as strand transfers or polymerization pauses during plus and minus strand synthesis and accurate formation of the central triplex (Klarmann et al., 1993; Charneau et al., 1994). This strongly suggests that central termination, the last event of lentiviral reverse transcription, occurs within an integral capsid structure. Central termination, which marks the end of viral DNA synthesis, could be a required signal for viral DNA decapsidation and its subsequent translocation into the nucleus.

These two putative molecular mechanisms for the DNA triplex mediated nuclear import of HIV-1 are not mutually exclusive. The formation of a central DNA triplex could trigger the maturation of viral capsids into PICs, thus making the DNA triplex accessible to shuttling proteins.

The fact that the integrity of the central DNA triplex is required for entry of the HIV-1 genome into the host cell nucleus implies that the entire process of DNA synthesis, including the last central strand displacement event, is completed prior to translocation of the HIV PIC through the nuclear pore. The subcellular distribution of lentiviral reverse transcription is currently under debate and whether HIV replication occurs in a specific cellular compartment is still an open question. On the basis of fractionation studies, it has been reported that HIV reverse transcription can occur entirely whin the cell nucleus (Bukrinsky et al., 1993a). However, fractionation techniques do not distinguish between an intranuclear localization and association with the nuclear membrane. Other authors have proposed on the contrary that association of the reverse transcription complex with the cytoskeleton is a prerequisite for viral DNA synthesis (Bukrinskaya et al., 1998). Kinetic studies of the synthesis of HIV-1 DNA and its association with the nuclear fraction indicate that the latter process is much more rapid than the former. The synthesis of HIV-1 DNA in the course of a single cycle of reverse transcription only reaches a plateau 24 to 48 hours following infection, whereas more than 95% of HIV-1 DNA fractionates with the nuclei of infected cells as early as 4 to 6 hours after infection (Barbosa et al., 1994). Therefore, we favor a third possibility that lentiviral reverse transcription takes place mainly in the immediate vicinity of the nuclear membrane and the NPCs, within the viral capsid, although further experiments will be necessary to confirm this hypothesis.

Cell mitosis does not provide an alternative pathway for the entry of triplex defective viral DNA into the host cell nucleus. The present Examples show that central triplex mutant viruses are strongly hampered in their replication capacity not only in non-dividing but also in dividing target cells. Conversely, insertion of a DNA triplex sequence in a HIV-1 based vector stimulates gene transduction in both dividing and non-dividing cells. This differs from the published phenotype of MA/Vpr mutant viruses, where a replication defect has been described exclusively in non-dividing cells (Bukrinsky et al., 1993b; Heinzinger et al., 1994; von Schwedler et al., 1994). Thus, MA/Vpr HIV mutants would behave like mitosis-dependent oncoviruses. One possible explanation for the different behavior of central triplex mutants is that these viruses are defective in a late step of the nuclear import process, consequently, the triplex deficient DNA molecules associate with the nuclear membrane. This close association persists during mitosis. The mutant viral DNA could be trapped within mitotic nuclear membrane vesicles, where it is unable to reach the cellular chromosomes, such as reported in the case of NLS-LacZ proteins (Bonnerot et al., 1987). Mutations in cellular NLS, inhibiting interactions with karyopherins, however, are known to induce cytoplasmic accumulation of the mutated protein (Kalderon et al., 1984; Lanford and Butel, 1984). Thus, mutations in the NLS sequences contribution to the karyophilic properties of HIV-1 PICs should induce cytoplasmic retention of the viral DNA, as previously suggested (Gulizia et al., 1994). It is therefore possible that PICs from MA/Vpr mutant viruses reach the cellular chromosomes following disruption of the nuclear membrane during mitosis. Nevertheless, there is as yet no direct experimental evidence for a mitosis dependent nuclear import pathway of lentiviral DNA genomes. As the published phenotype of MA/Vpr mutant viruses must be viewed with some caution, the same caution must be applied to the starting hypothesis that a nuclear import deficiency in lentiviruses should lead to a replication defect exclusively in non-dividing cells. Whether lentiviruses can adopt a mitosis dependent nuclear import strategy, or whether the active nuclear import of lentiviral genomes occurs in both dividing and non-dividing cells, remains an open question.

The present invention provides designs for lentiviral vectors. Since the infection of non-dividing target cells by lentiviruses relies on their use of an active nuclear import pathway, it is important to maintain the lentiviral nuclear import determinants in derived vector constructs. Classical retroviral vector constructs are replacement vectors in which the entire viral coding sequences between the LTRs are deleted and replaced by the sequences of interest. In the case of lentiviral vectors, this classical strategy leads to the deletion of the central cis-active sequences cPPT and CTS. The important role of the triplex in HIV nuclear import implies that such replacement vector constructs are not optimal. Thus, insertion of the HIV DNA triplex into the HR GFP replacement vector (Naldini et al., 1996) enhanced its gene transduction efficiency by complementing a nuclear import defect of the HR vector genome to a rate of DNA import close to that of wild type HIV-1.

It is noteworthy that while HIV vectors lacking a DNA triplex were still capable of gene transduction (FIGS. 2C, 2D), the residual replication of viruses mutated in cPPT is absent or extremely low (FIGS. 6A, 6B). One possible explanation is that triplex independent nuclear import could occur in the case of a small vector genome (about 4 kb for HR-GFP), but the presence of a DNA triplex would be required for the import of the 9.7 kb native HIV-1 genome. In fact, active, if relatively inefficient, nuclear import of DNA molecules as large as 3 to 4 kb has been reported (Hagstrom et al., 1997).

The cis-active sequences responsible for formation of the DNA triplex are found at the center of all lentiviral genomes. This central position could have evolved on account of its structural implications for the conformation of PICs, in so far as symmetrical folding of the left and right arms of the linear DNA molecule around the triplex might be necessary for its efficient uptake through the NPCs (FIG. 7B). If this is true for the virus, then a central position of the DNA triplex might also be required for the efficient nuclear import of vector genomes.

EXAMPLES

The invention will be further clarified by the following examples, which are intended to be purely exemplary of the invention.

Example 1

Experimental Procedures

Cells

MT4 cells are HTLV-1 transformed human CD4+ T cells that allow acute cytopathic HIV-1 infection (Harada et al., 1985). H9 cells are less permissive to HIV but allow chronic production after infection. MT4 and H9 cells were maintained in RPMI 1640 medium supplemented with 10% fetal calf serum (FCS). Peripheral blood lymphocytes (PBLs) were obtained from healthy donors, stimulated with 1 μg/ml of phytohemagglutinin (Wellcome), and maintained in the presence of Interleukin-2 (10% lymphocult; Biotest Diagnostics). 293T cells were grown in DMEM medium supplemented with 10% FCS. P4 indicator cells are HIV infectible HeLa CD4+ cells carrying the LacZ gene under the control of the HIV-1 LTR (Charneau et al., 1994). P4 cells are grown in DMEM medium supplemented with 10% FCS and 500 µg/ml of G418.

Collection and Fractionation of Cells.

Cord Blood samples were collected with the informed consent of the mothers. CD34+ cells were purified as previously described (Robin, C. et al., 1999) using miniMACS immunomagnetic bead separation system (Milteny Biotec). The purity of bead-separated CD34+ cells was over 75%. CD34+CD38lo/-fractions were further purified by cell sorting with a FACS Vantage™ equipped with an argon ion laser (Becton Dickinson), using murine monoclonal antibodies (MoAbs) directed against CD34-PE-Cy5 (Immunotech) and CD38-PE (Becton Dickinson). CD34+ cells were either frozen in fetal calf serum (FCS, Stem Cell) containing 10% DMSO (Sigma) or used immediately.

DNA Constructs

Proviral Plasmids:

Site directed mutagenesis was performed as previously described (Kunkel, 1985) in M13 mp18 carrying an EcoRI 1.1 kb insert (4684 to 5779) from the infectious molecular clone pLAI3. Mutagenic primers were as follows:

```
cPPT-AG
                              (SEQ ID NO: 1)
5' pCAATTTTAAAAGAAGAGGGGGGATT 3' cPPT-D:
                              (SEQ ID NO: 2)
5' pATTCATCCACAACTTCAAGCGCCGCGGT

GGTATTGGGGGGTAC 3'.
``` pcPPT-AG, pcPPT-D, pcPPT-25 and pCTS were constructed by cloning back the mutated EcoRI fragment into pLAI3.

Vector Plasmids:

Vector plasmids were derived from HR'CMVLacZ (Naldini et al., 1996). The LacZ reporter gene was replaced by the EGFP gene (Clontech). EGFP gene was amplified by PCR using Pfu polymerase (Stratagene) from pEGFP-N1 plasmid, adding BamHI and XhoI restriction sites at the 5' and 3' ends respectively. PCR primers were as follows:

```
Bam GFP:
                              (SEQ ID NO: 3)
5' CC GGATCC CCA CCG GTC GCC ACC 3'

Xho GFP:
                              (SEQ ID NO: 4)
5' CC CTCGAG CTA GAG TCG CGG CCG 3'.
```

The HR GFP vector was constructed by cloning back this PCR fragment into the BamHI and XhoI sites of pHR'CMVLacZ, replacing the LacZ ORF with EGFP.

TRIP ΔU3 CMV GFP and TRIP ΔU3 PL CMV GFP:

First, a subclone containing a unique LTR was constructed and named pUC LTR. The KpnI/XbaI fragment of TRIP GFP encompassing its 3'LTR was cloned into pUC18. Then the EcoRI site was destroyed by filling in, creating the vector pUC LTR RI–. Diverging PCR was performed on pUC LTR RI– with the aim of amplifying the whole plasmid except the promoter and the enhancer of the U3 sequence. The primers were:

```
DU3-:
                              (SEQ ID NO: 5)
5' CGGAATTCGGATCCGCGGCCGCATCGATCTTGTCTTCGTTGGG

AGTG 3'

DU3+:
                              (SEQ ID NO: 6)
5'CGGAATTCAGCCGTCTCGAGAGATGCTGCATATAAGCAGC 3'.
```

The primers contain the restriction sites to be inserted instead of the U3 sequence including the EcoRI site present on each primer. The PCR product was digested with EcoRI then used to transform competent bacteria. The plasmid constructed thereby was named pLTR ΔU3 RI–. The polylinker inserted instead of theU3 sequence in pLTR ΔU3 RI– is: ClaI-NotI-BamHI-EcoRI-MluI-XhoI.

The TRIPΔU3 PL GFP plasmid was constructed by replacing the KpnI/NheI fragment of TRIP GFP containing the 3' LTR with the KpnI/XbaI fragment of pLTR ΔU3 RI– (NheI and XbaI restriction products are compatible). Then the polylinker (PL) was deleted from pLTR ΔU3 RI– by digestion with ClaI/XhoI and filling in.

The TRIP ΔU3 GFP plasmid was constructed by exchanging the KpnI/NheI fragment of TRIP GFP with the KpnI/XbaI fragment of pLTR U3 APL RI–.

A 178 bp fragment of pLAI3 (4793 to 4971), encompassing cPPT and CTS, was amplified by PCR. NarI restriction sites were added in 5' of the primers with the aim of inserting this fragment into the unique ClaI site of HR GFP:

```
Nar TRIP+:
                              (SEQ ID NO: 7)
5' GTG GTC GGCGCC GAATTC ACA AAT GGC AGT ATT CAT

CC 3'

Nar TRIP-:
                              (SEQ ID NO: 8)
5' GTC GTC GGCGCC CCA AAG TGG ATC TCT GCT GTC C 3'
```

Insertion of this triplex sequence in the correct orientation gave rise to the TRIP GFP plasmid vector, and TRIPinv GFP in the reverse orientation. Alternatively, the same triplex fragment was amplified from pcPPT-AG, pcPPT-D, pcPPT-225, and pCTS plasmids to generate vectors including the same mutations in the cPPT or in the CTS as the corresponding viruses.

TRIP EF1α GFP and TRIP ΔU3 EF1α GFP:

The CMV promotor of TRIP GFP was replaced by the EF1α promotor. The triplex sequence and the EF1α promotor were first amplified separately, with overlapping primers. The triplex sequence was amplified with the primers Nar TRIP+ and Mlu TRIP– on the matrix pLai and the EF1α promotor was amplified on the matrix pEFpgkneo with the primers Mlu EF1+ and Bam EF1–.

```
Nar TRIP+:
                              (SEQ ID NO: 9)
5'GTC GTC GGCGCC GAATTC ACA AAT GGC AGT ATT CAT

CC 3'

MluTRIP-:
                              (SEQ ID NO: 10)
5'AGC CTC ACG ACGCGT AT CAG CCA AAG TGG ATC TCT

GCT G 3'
```

-continued

Mlu EF1+:
(SEQ ID NO: 11)
5' CTG AT ACGCGT CGT GAG GCT CCG GTG 3'

Bam EF1-:
(SEQ ID NO: 12)
5' CG GGATCC TGT GTT CTG GCG GCA AAC3'

Then a second round of PCR was performed on a mixture of the first two PCR products, using the external primers Nar TRIP+ and Bam EF1-. The triplex sequence and the EF1α promotor stuck together by this technique.

Plasmid TRIP EF1α GFP was constructed by replacing the EcoRI/BamHI fragment of TRIP GFP containing the triplex sequence and the CMV promotor by the PCR product TRIP EF1α digested with EcoRI/BamHI (the Nar TRIP+ primer posses a EcoRI site in its 5' end).

To construct the TRIP ΔU3 EF1α GFP plasmid, the EcoRI/BamHI fragment of TRIP EF1α GFP containing the triplex sequence and the EF1α promotor was inserted in TRIP ΔU3 GFP instead of the EcoRI/BamHI fragment containing the triplex sequence and the CMV promotor.

Virus and Vector Production

For the investigations reported in FIGS. 1-6, viruses were produced by transient transfection of HeLa cells by the calcium phosphate co-precipitation technique. Vector particles were produced by transient co-transfection of 293T by the vector plasmid, and encapsidation plasmid (p8.2) and a VSV envelope expression plasmid (pHCMV-G, (Yee et al., 1994)), as previously described (Naldini et al., 1996). All virus and vector supernatants were treated with DNaseI (1 µg/ml in the presence of 1 µM MgCl$_2$) for 15 minutes at 37° C.

Lentiviral Vector Particle Production

For the investigations reported in FIGS. 7-9, viruses were produced by transient co-transfection of 293T by the vector plasmid, an encapsidation plasmid (p8.2) and a VSV envelope expression plasmid (pHCMV-G, (Yee et al., 1994)), as previously described (Naldini et al., 1996). All virus and vector supernatants were treated with DNaseI (1 µg/ml in the presence of 1 µM MgCl2) for 15 minutes at 37° C.

Virus and Vector Titrations

For the investigations reported in FIGS. 1-6, one cycle titration of viruses were performed in triplicate by infection of P4 cells plated in 96 well plates, with equivalent amounts of particles (1 ng of p24 viral antigen per well), in the presence of 20 µM of DEAE-dextran. The protease inhibitor Saquinavir (Roche), was added (1 µM) throughout the experiment, to restrict the analysis to a single cycle of infection. Cell mitosis was inhibited by aphicolin treatment (8 µM), the day prior to infection. The β-Galactosidase activity was measured 48 hours after infection using a chemiluminescent β-Gal reporter gene assay (Boehringer).

HeLa cells were infected in triplicate with equivalent amounts of vector particles (5 ng P24 per well). At 48 hours post transduction, the medium was replaced by 200 µl of TNB (Tris 50 mM pH 7.5, NaCl 150 mM) and fluorescence of living cells was quantitated using a microplate fluorimeter (Victor$^2$, Wallac) and EGFP adapted filters (excitation: 485 nm, emission: 520 nm).

Transduction Protocol

For the investigations reported in FIGS. 7-9, 24- or 96-well tissue culture plates were coated with fibronectin (Bio-Whittaker Europe) according to the manufacturers instructions. Human CD34+ populations were plated, immediately after purification or thawing, at 2 to 3×10$^5$ cells/ml in serum free medium (IMDM containing 11.5 µM a-thioglycerol, 1.5% BSA (both from Sigma), sonicated lipids and iron-saturated human transferrin) or a-MEM containing 10% FCS in presence of 4 µg/ml of polybrene (Sigma) and 4 recombinant (r) human (hu) cytokines: rhu-Stem Cell Factor (SCF, 100 ng/ml, provided by Amgen), Flt3-Ligand (FL, 100 ng/ml, Diaclone), IL-3 (60 ng/ml, Sandoz), and pegylated-(PEG-) rhu-Megacaryocyte Growth and Differentiation Factor (MGDF) (10 ng/ml, Amgen), and concentrated lentiviral virus at the concentration of 100 ng of viral P24/ml during 24 hours. Cells were then washed and cultured in lympho-myeloid conditions (in culture tissue culture plates precoated with MS5 cells in RPMI supplemented with 10% human serum, 5% FCS and the following 7 cytokines: rhu-SCF (50 ng/ml), rhu-FL (50 ng/ml), PEG-rhu-MGDF (50 ng/ml), rhu-IL-3 (10 ng/ml), rhu-IL-2 (5 ng/ml), rhu-IL-15 (10 ng/ml), and rhu IL-7 (20 ng/ml) (the three IL-being from Diaclone) for 48 hours. Then, expression of eGFP in the CD34+ cell fraction was evaluated using a CD34-PE-Cy5 MoAb (Immunotech). Analysis was done on a FACS Scan using the Cellquest software (Becton Dickinson).

Clonogenic and Long Term Culture (LTC) Assays

Clonogenic progenitors from human fresh CB cells were assayed in 0.8% methylcellulose containing 30% FCS, 1% deionized BSA, and 10-4M 2-mercaptoethanol, in the presence of 50 ng/ml rhu-SCF, 10 ng/ml rhu-GCSF (Amgen), 2 ng/ml rhu-IL3, and 2 U/ml rhu-EPO (Amersham). Bone marrow (BM) cells from engrafted NOD-SCID mice were plated in the presence of rhu-SCF, -IL-3, -EPO, and -GM-CSF (10 ng/ml) as described (Pflumio, F. et al., 1996). Progenitors were scored on day 14-16 according to criteria already described (Croisille L. et al., 1994) and EGFP expression observed by fluorescent microscopy using a Nikon Eclipse TE300 microscope. Long Term Culture (LTC) was performed as previously described (Issaad C. et al., 1993) either in limiting dilution in 96-wells plates using the FACS vantage equipped with an ACDU (BD) or in bulk culture in 24-wells plates containing a confluent layer of the murine stromal cell line MS5. After 5 to 10 weeks, adherent and non-adherent cells were harvested and plated for the clonogenic assay. For both clonogenic and LTC-IC assays, colonies were picked individually and frozen before PCR analysis.

PCR Analysis

PCR analysis was performed on genomic DNA obtained either from colonies derived from clonogenic progenitors or from clones grown in lympho-myeloid cultures. Cells were lysed and proteins were digested in 20 µl of buffer containing proteinase K (10 µg/ml), KCl (50 mM), Tris-HCl (10 mM, pH 8.3), MgCl$_2$ (2.5 mM), gelatin (0.1 mg/ml), NP40 (0.45%), and Tween 20 (0.45%). Amplification of genomic DNA was performed with the sense primer 5' CCCTCGAGCTAGAGTCGCGGCCG 3' (SEQ ID NO:13) and the antisense primer 5' CCGGATCCCCACCGGTCGCCACC 3' (SEQ ID NO:14) at the annealing temperature of 62° C. The amplification resulted in an 800 bp product.

Viral and Vector DNA Analysis

P4 or MT4 cells were infected at a high multiplicity of viruses (150 ng of p24 per 10$^6$ cells) or transduced by vectors (25 ng of p24 per 10$^6$ cells), in the presence of 20 µg/ml of DEAE-dextran in the case of P4 cells. DNA from infected or transduced cells was extracted at various times, restricted, and analyzed by Southern blot. In all cases, contaminating bacterial plasmid DNA was removed from the analysis by DpnI digestion. DNA from infected cells was digested by MscI and XhoI and DNA from transduced cells by EcoNI, AvaII and XhoI. After electrophoresis and transfer of 10 µg of digested DNA, membranes were hybridized with random primed [$^{32}$P]-labeled DNA probes (Rediprime II, Amersham). Virus specific DNA probe was amplified by PCR from pLAI3 plasmid template using the following primers:

```
5Msc:
                                            (SEQ ID NO: 15)
5' AGA AGA AAT GAT GAC AGC ATG 3'

3Msc:
                                            (SEQ ID NO: 16)
5' TGC CAG TTC TAG CTC TG 3'.
```

The resulting 1680 bp DNA fragment (from position 1818 to 3498 of pLAI3) overlaps the MscI restriction site at position 2655 of viral genomes.

Vector probe was synthesized by PCR on pTRIP GFP with the primers:

```
5EcoNI:
                                            (SEQ ID NO: 17)
5' CAG GGA CTT GAA AGC GAA AG 3'

3EcoNI:
                                            (SEQ ID NO: 18)
5' GCT TGT GTA ATT GTT AAT TTC TCT GTC 3'
```

The vector probe is a 1027 bp fragment (from position 649 to 1676 of pTRIP GFP) and overlaps the EcoNI site at position 1156 of vector genomes.

To assay the amount of retrotranscribed DNA from wild type and PPT-AG and cPPT-D viruses, a similar protocol was followed except that the DNA extracted at 12 hours post-infection was restricted by MscI and DpnI. The probe used for hybridization was the MscI 1.9 kb internal fragment from pLAI3. Hybridization signals were quantitated using a phosphorimager (Molecular Dynamics) and the ImageQuant software.

In Situ Hybridization

P4 cells were infected at a high multiplicity (2 μg of p24 antigen of each virus per $10^6$ cells), in the presence of 20 μg/ml DEAE dextran. At 24 hours post-infection, cells were trypsinized, extensively washed (in order to remove viral particles adsorbed in the plasma membrane), and re-plated on glass cover slides in 24 well plates. Cells were grown for a further 48 hours and fixed in 4% PFA/PBS for 20 minutes at room temperature. Cells were washed in PBS and permeabilized by 0.5% Triton/0.5% Saponin in PBS, for 5 minutes at room temperature. Dehydrated samples were treated with RNase A (200 μg/ml in 2×SSC), one hour at 37° C. and by proteinase K (6 μg/ml in PBS), about 5 minutes. Samples were denatured by incubation in 70% deionized formamide/2×SSC for 2 minutes at 70° C. followed by 30% deionized formamide/2×SSC for 2 minutes at 70° C. Hybridizations were performed overnight at 37° C. using a nick translated biotynilated pLAI3 plasmid (50% deionized formamide, 10% dextran sulfate, 10 μg/ml Salmon sperm DNA, 0.1% Tween 20 in 2×SSC). Samples were extensively washed (serial washing in 2×SSC/50% formamide at room temperature and then at 50° C.). Detection of hybridized probes was performed using the Tyramid-Streptavidin TSA-Direct kit (NEN) according to the manufacturer's instructions.

Example 2

Central Initiation of Reverse Transcription is an Essential Step of the HIV-1 Replicative Cycle In a previous work, we showed that conservative mutations in the cPPT and CTS sequences severely impaired virus replication (Charneau et al., 1992; Hungnes et al., 1992). A central initiation mutant virus (cPPT-225) and a termination mutant virus (CTS) showed respectively four fold and ten fold decreased infectivity in one round titration experiments. In order to inactivate the function of the cPPT, semi-conservative mutations were introduced in the overlapping integrase coding region. In the mutant virus cPPT-D, the lysine to arginine change at position 188 allowed the introduction of a total of 10 mutations into the 19 nucleotide sequence of the PPT primer (FIG. 1A) (Huber and Richardson, 1990). The effect of this amino acid change on virus replication was checked by construction of the control cPPT-AG mutant virus, in which a single mutation from purine to purine, respecting the polypurine nature of cPPT, induced the same amino acid change. The presence of a DNA triplex in retrotranscribed wild type and cPPT-AG viruses DNA, and its absence from cPPT-D virus DNA, was confirmed by S1 nuclease cleavage of Hirt DNA from infected cells as previously described (Harris et al., 1981; Charneau and Clavel, 1991).

Figure 1B:
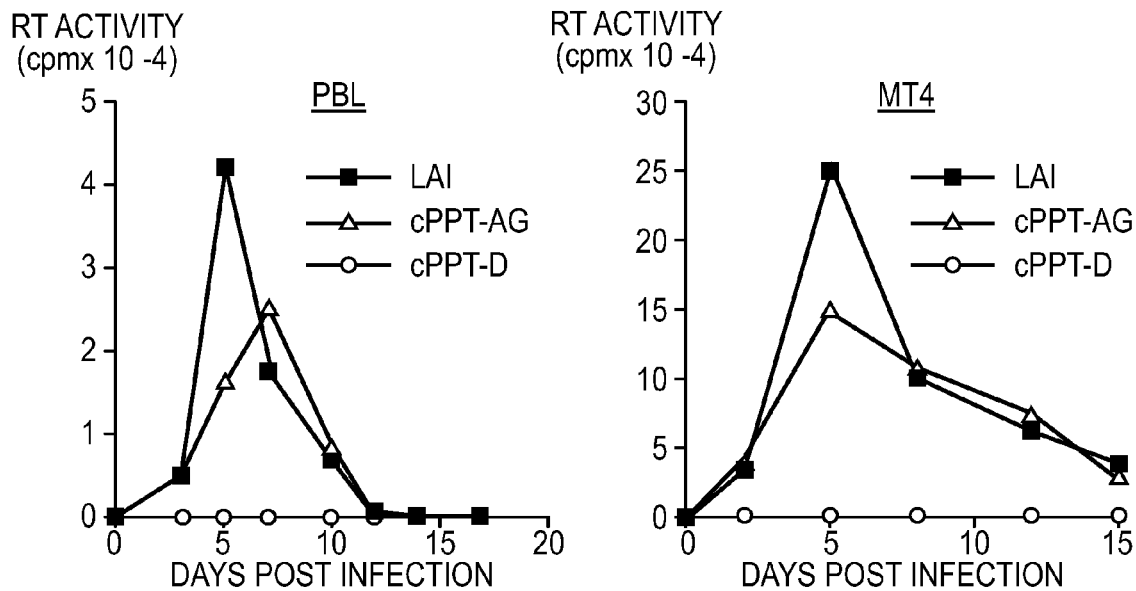

Virus infectivity was first evaluated in classical kinetic replication experiments in cell cultures. PHA stimulated peripheral blood lymphocytes (PBLs) and MT4 cells were infected with equal numbers of viral particles, normalized according to the capsid protein (p24) content of the viral supernatants, and reverse transcriptase activity was followed over time in the culture supernatants (FIG. 1B). Growth curves of the wild type HIV-1 LAI and cPPT-AG control viruses were similar in both cell systems. The fact that the K188R mutation occurs naturally in some HIV-1 isolates, already suggested that it has little or no effect on the integrase and PPT functions. In contrast, when PBLs were infected with the cPPT-D mutant virus, no replication was detected during the 15 days of culture. The same was true for MT4 cells, despite their high susceptibility to HIV infection. The cPPT-D mutant virus was also non infectious in immortalized cell lines such as H9 or CEM (data not shown).

Figure 1C:
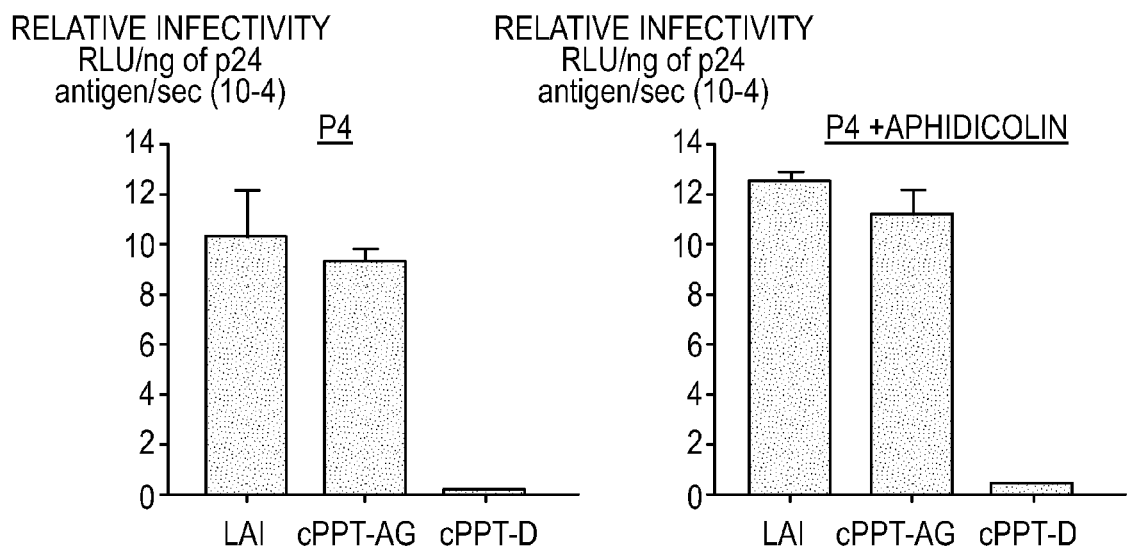

Virus infectivity was then quantitatively analyzed by titrations based on a single round of replication (FIG. 1C). P4 indicator cells (HeLa CD4 LTR-LacZ) (Charneau et al., 1994) were infected with equivalent numbers of virus particles of the different viruses. These one cycle titrations confirmed the almost complete loss of infectivity of the cPPT-D mutant virus. In P4 cells, infectivity of the cPPT-AG control was identical to that of the wild type virus, whereas infectivity of the cPPT-D mutant was strongly reduced, to levels close to background. The same results were obtained in aphidicolin treated, non dividing P4 cells (FIG. 1C, right panel).

These findings strongly suggest that the central initiation of reverse transcription is necessary for HIV replication in non dividing as well as in proliferating cells.

Example 3

Virus Production is not Affected by Mutations in cPPT

Figure 2A:
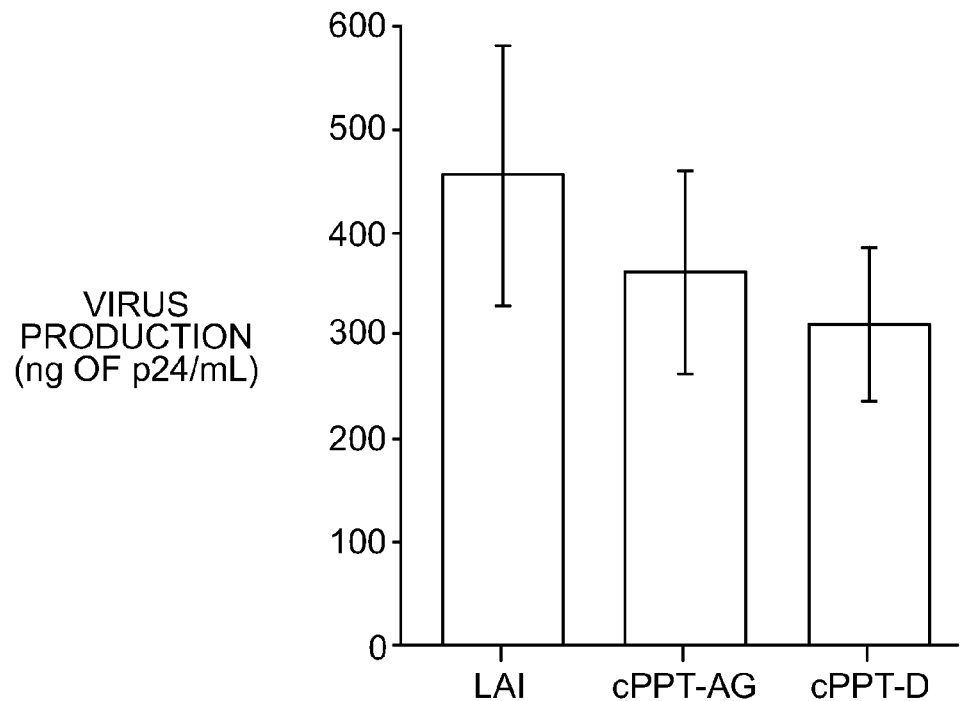

We checked that the different mutations introduced into the cPPT-AG and cPPT-D plasmid proviruses did not affect the late steps of the replicative cycle. Virus production was quantified, according to the P24 content of the supernatants, after transient transfections of HeLa cells by proviral plasmids. The production of the cPPT mutant viruses was found not to be significantly different from that of the wild type virus (FIG. 2A). Hence the mutation K188R does not affect the late phase of HIV-1 replication. Therefore, the defective step involved in the phenotype of the cPPT-D mutant virus must precede the expression of viral DNA and belong to the early phase of the HIV replicative cycle.

Example 4

Figure 2B:
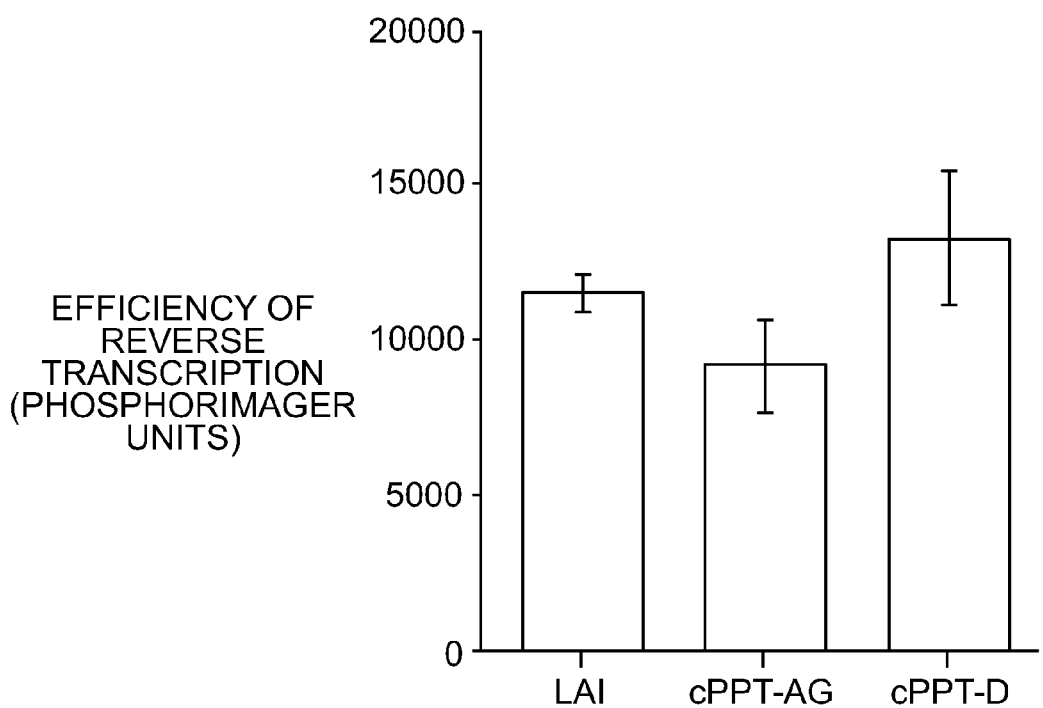

Mutations in the cPPT do not Affect the Rate of Reverse Transcription of HIV-1 Genome The effect of mutations in cPPT on viral DNA synthesis was evaluated by quantifying the DNA synthesized in a single round of retrotranscription (FIG. 2B). An internal MscI restriction fragment from the viral DNA of infected cells was detected by Southern blotting and quantitated, using the corresponding MscI DNA fragment as a probe. Since the internal MscI fragment is common to the integrated proviral DNA and the unintegrated linear and circular molecules, its quantitation reflects the total amount of viral DNA, irrespective of its integrated or unintegrated state. To limit the analysis to the first cycle of reverse transcription, DNA from infected P4 cells was harvested 12 hours after infection, before initiation of a second round of infection. The total amount of DNA retrotranscribed in a single cycle of reverse transcription was the same after infection with the cPPT-D mutant, the cPPT-AG control or the wild-type virus. These experiments showed that, whereas mutations in cPPT abolish virus replication, they do not affect the rate of DNA synthesis. The replicative defect of cPPT mutant viruses implicates a step subsequent to viral DNA synthesis.

Example 5

Lack of a Central DNA Triplex does not Affect the In Vitro Integration of HIV-1 PICs The in vitro integration ability of PICs from wild-type HIV-1 and central initiation mutants was compared (FIG. 2C) using a quantitative in vitro integration assay as described by Farnet (Farnet and Haseltine, 1990), with minor modifications. Since HIV-1 replication complexes reside only transiently in the cytoplasm of freshly infected cells (Barbosa et al., 1994), the preparation of sufficient amounts of HIV PICs requires massive infection and cellular fractionation within 4 to 6 hours. This was achieved by co-culture of H9 cells chronically infected by either wild type or cPPT-225 virus and uninfected HUT 78 target cells. The cPPT-0225 mutant virus (FIG. 1A) was chosen for these experiments instead of the non infectious cPPT-D, which is unable to establish a chronic infection. The residual infectivity of cPPT-225 mutant virus is low but sufficient to allow it to slowly propagate in cell cultures (Charneau et al., 1992).

HIV PICs were isolated from the cytoplasm of infected cells and incubated in the presence of a linearized Bluescript plasmid target DNA. Integration was revealed by the presence of a 12.7 kb fragment, reactive to the HIV-1 probe, corresponding to the expected size of the 9.7 kb linear HIV genome integrated into the 3 kb target DNA.

Figure 2C:
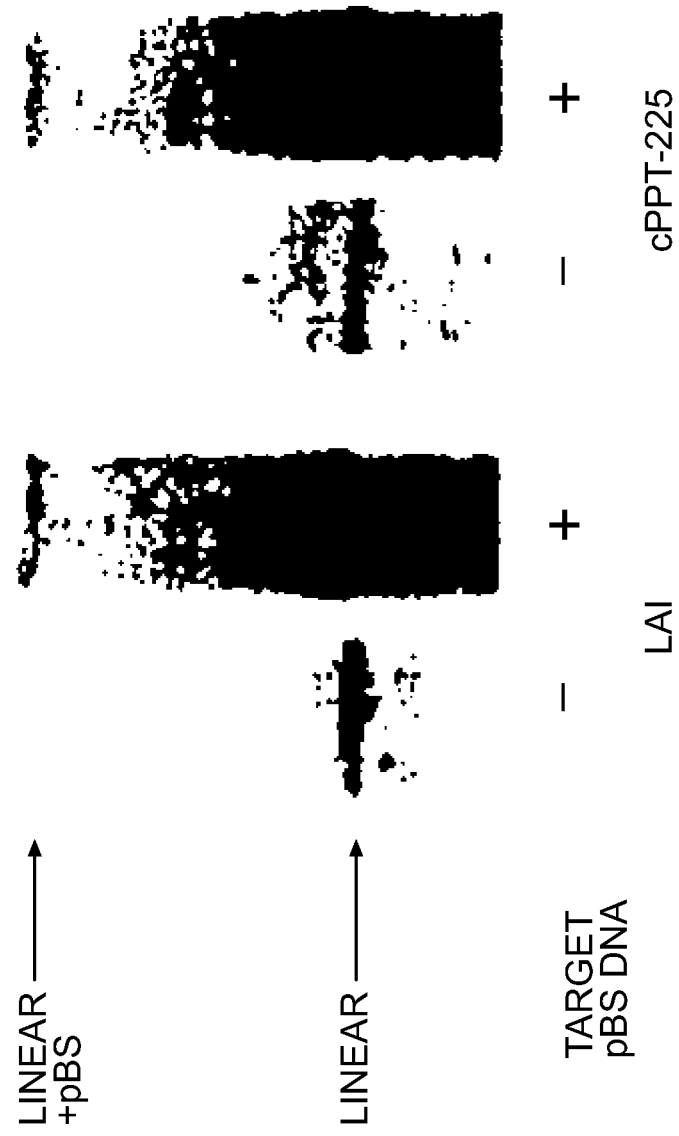

The amount of linear DNA integrated into the plasmid DNA did not differ between the wild type and cPPT 225 mutant virus (FIG. 2C). Hence HIV-1 PICs from the cPPT mutant retained their full ability to integrate in vitro. The defective replication step of central DNA triplex mutant viruses must lie after reverse transcription but before integration of their linear HIV genome into the host cell chromatin.

Example 6

Impaired Nuclear Import of Central DNA Triplex Mutant Viruses

The foregoing experiments suggested that the replicative defect of central DNA triplex mutant viruses was related to the access of HIV PICs to chromatin of the cellular target. Hence we tested the hypothesis of a nuclear import defect of DNA from cPPT mutant viruses. Studies on the nuclear import of HIV-1 PICs are hampered by lack of a quantitative and reproducible assay for nuclear import at the level of the viral DNA. Once retrotranscribed in the cytoplasm, the retroviral linear DNA is imported into the nucleus where it either integrates or circularizes. Unintegrated retroviral DNA circles, containing one or two LTRs, are found exclusively within the nucleus, and thus represent convenient markers of viral DNA nuclear import. To assess HIV DNA nuclear import, previous studies used PCR amplification of two unintegrated LTR DNA circles. However, as reported herein and by Barbosa et al., (1994), because two LTR circles represent a minute fraction of the HIV DNA in infected cells, their detection is very sensitive to minor alterations of cell physiology or virus infectivity. Therefore, we designed a novel assay which permits a quantitative follow-up by Southern blot of the synthesis, circularization, and integration of HIV DNA.

Figure 3A:
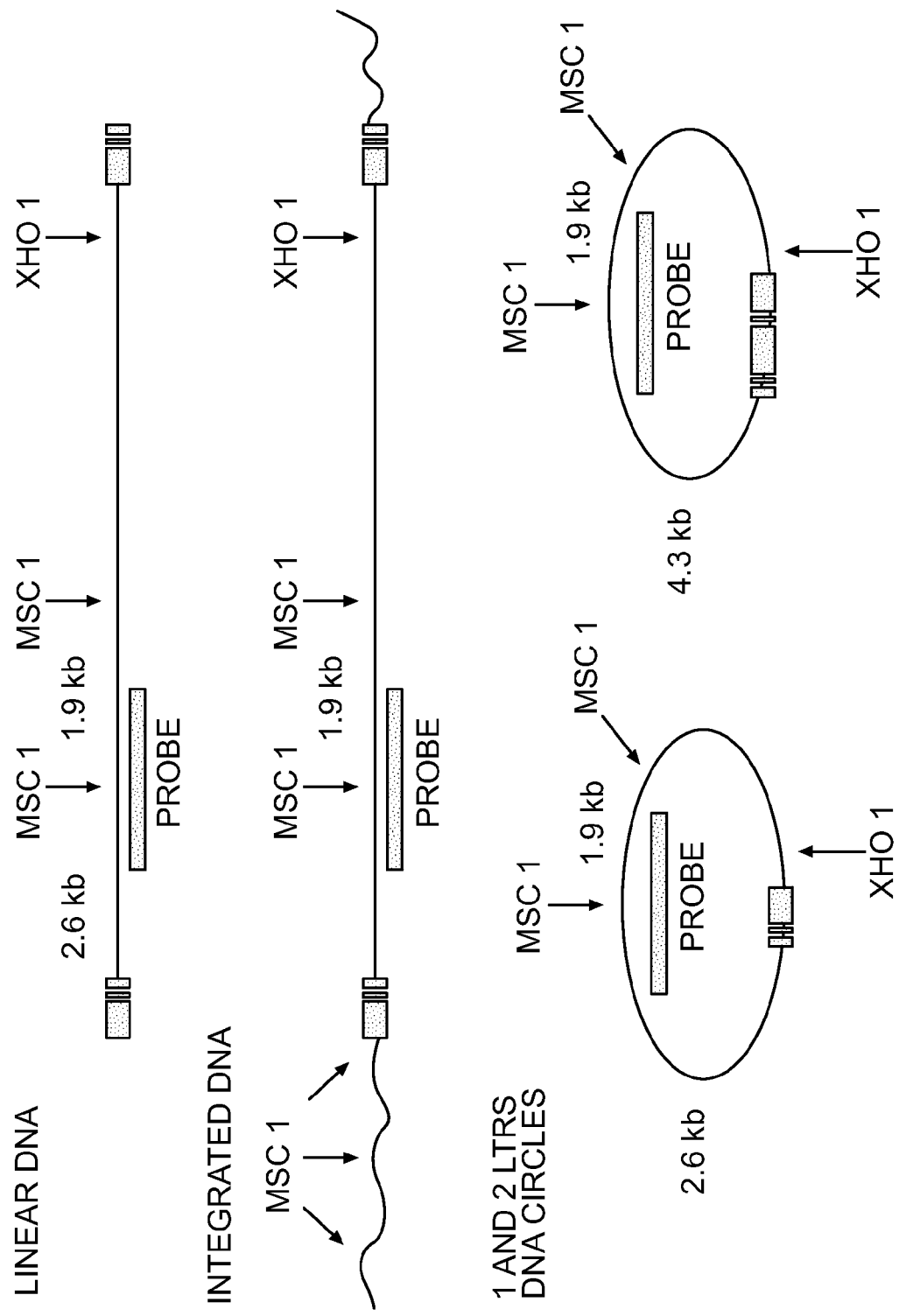

Briefly, DNA from infected cells is prepared at various time points and digested with MscI, a restriction enzyme which cuts the HIV-1 genome twice. Using a PCR generated DNA probe exactly overlapping the 5' MscI site, several specific bands are revealed (FIG. 3A). The internal 1.9 kb MscI fragment is common to all viral DNA species irrespective of their integrated or unintegrated state and quantitation of this band indicates the total amount of viral DNA in infected cells. A 2.6 kb band corresponds to the distal 5' MscI fragment of unintegrated linear HIV-DNA. To minimize transfer bias due to the large size of DNA circles specific fragments, the DNA is further cut with XhoI. One and two LTR circular DNA then appears at 2.8 and 3.4 kb bands respectively. Since the DNA probe exactly overlaps the 5' MscI site, the intensity of each band is directly proportional to the quantity of the corresponding viral DNA species. The amount of integrated proviral DNA is calculated by subtracting from the total amount of viral DNA the signals of unintegrated linear and circular viral DNAs. A parallel quantitation of the same infected cell population was performed after a Hirt fractionation to separate low molecular weight unintegrated viral DNA from high molecular weight integrated proviral DNA. This gave rise to identical results, thus validating the one step subtractive calculation.

As indicated by the kinetics of accumulation of total viral DNA (1.9 kb internal fragment), the synthesis of viral DNA proceeded for 24 to 48 hours after infection, reflecting an asynchronous infection process. The amounts of total viral DNA from cPPT-AG and cPPT-D mutant viruses were similar to those of wild-type HIV-1. As previously, the mutations in cPPT did not influence the rate of DNA synthesis. Detectable amounts of full length unintegrated linear DNA were present in cells as early as 6 hours after infection (FIG. 3B). Integrated proviruses and DNA circles were first detected 12 hours after infection. Integration and circularization proceeded to completion over a further 36 hours.

On completion of one cycle of infection, in the case of the wild type virus, about 55% of the viral DNA had integrated into the host cell DNA, about 35% had circularized into one LTR circle, and a small fraction of less than 10% remained in the form of stable unintegrated linear DNA (FIG. 3C). Notably, two LTR circular DNA, although detectable at 48 hours after infection, was present only in trace amounts. DNA from the cPPT-AG control virus was processed in a very similar manner to DNA from the wild type virus.

In the case of the cPPT-D mutant virus, a marked alteration in the pattern of intracellular viral DNA was evident, with a clear and persistent accumulation of unintegrated linear molecules. At 48 hours after infection, only very small amounts of one LTR circular DNA and integrated proviral DNA had been generated and more than 90% of the cPPT-D mutant DNA remained blocked in the unintegrated linear form (FIG. 3C).

A nuclear import defect is expected to decrease the proportion of nuclear viral DNA species (integrated proviruses and one and two LTR circles) and to concomitantly increase the proportion of untranslocated linear DNA molecules. Thus, the intracellular DNA profile of cPPT-D mutant virus strongly suggests a defect of viral DNA nuclear import.

Example 7

Linear DNA from Central DNA Triplex Mutant Viruses Accumulates at the Vicinity of the Nuclear Membrane To further characterize the nuclear import defect of central DNA triplex mutant viruses, we addressed the questions of whether the mutated linear DNA molecules accumulate in a particular subcellular compartment. The nuclear import process can be divided into two main phases, docking of the nuclear component to the nuclear membrane and its translocation through the nuclear pore complex (NPC). We first conducted classical nuclei/cytoplasm fractionation of infected cells, followed by southern blot detection of viral DNA. The totality of viral DNA of all viruses was associated with the nuclei of infected P4 cells, 24 hours after infection (FIG. 4A), suggesting that docking of HIV DNA to the nuclear membrane was not affected by the lack of a central DNA triplex.

Figure 4B:
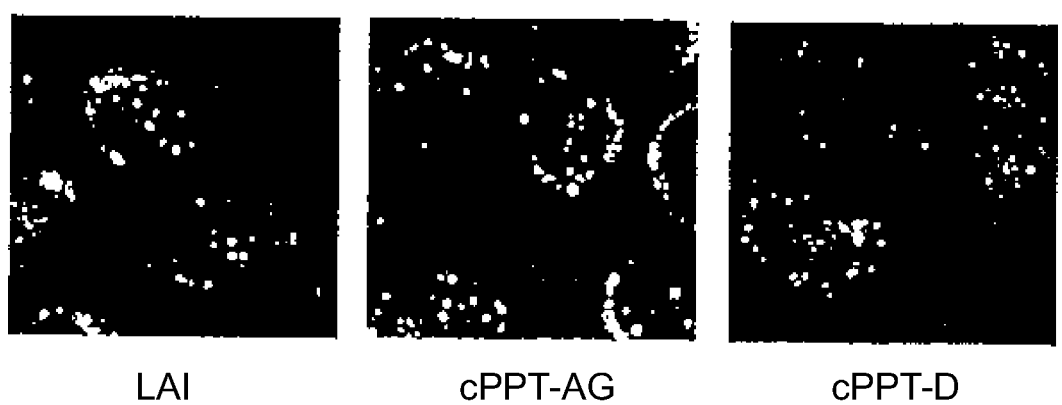

To confirm that central triplex deficient DNA molecules do accumulate at the nuclear membrane, we used fluorescent in situ hybridization (FISH) to directly visualize the intracellular location of HIV genomes. P4 cells were infected at a high multiplicity in one cycle conditions, hybridized with a full length HIV-1 genome probe, and observed by deconvolution microscopy. Specific dots were found predominantly within the nucleus in the case of the wild type and cPPT-AG control viruses (FIG. 4B). Since FISH cannot distinguish between the different HIV DNA species, these intranuclear viral DNA molecules could have been integrated proviruses or unintegrated DNA circles. Some rare genomes were associated with the nuclear membrane and probably represented the residual linear DNA detected by Southern blotting at the same time after infection. Other dots associated with the plasma membrane most likely derived from membrane adsorbed defective particles containing partially retrotranscribed genomes (Lori et al., 1992). In contrast, HIV genomes were predominantly localized at the nuclear membrane and almost completely absent from the nucleus in the case of the cPPT-D mutant virus. As the Southern blot DNA profile indicated that practically all cPPT-D DNA was blocked in the linear form, we can assume that these HIV genomes associated with the nuclear membrane were unintegrated linear DNA molecules. This direct visualization of viral DNA molecules in infected cells confirmed the association of the viral DNA of central triplex mutants with the nuclear membrane.

Our FISH experiments suggest that cPPT mutant viruses are defective in the translocation of their genome through the NPCs. Nevertheless, the clear demonstration of a translocation defect, by localization of mutant viral DNA at the cytoplasmic side of NPCs, is not accessible through FISH experiments.

Altogether, we conclude from these results that the central DNA triplex of HIV-1, created by central initiation and termination steps during reverse transcription, is important for HIV-1 PICs to enter the host cell nucleus. In the absence of DNA triplex, viral DNA nuclear import is severely impaired at a stage immediately preceding or during the translocation of HIV-1 DNA through the nuclear pore.

Example 8

Figure 5A:
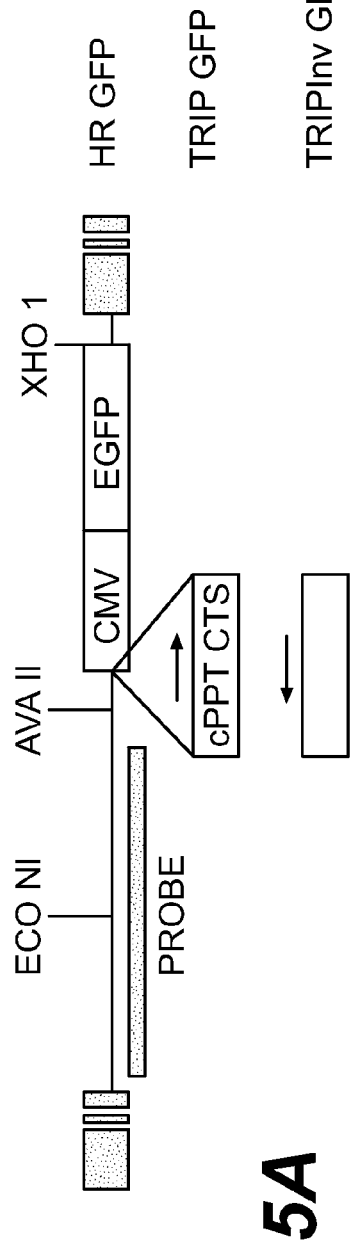

Impact of the Central DNA Triplex on Gene Transduction by an HIV-1 Based Vector System Having identified the central DNA triplex as a key determinant for the nuclear import of HIV-1, we tested the effect of inserting the central cis-active sequences of HIV-1 into the previously described HR HIV-1 vector (Naldini et al., 1996) (FIG. 5A). To monitor gene transduction, a gene encoding the green fluorescent protein (GFP) was further inserted. The vector containing a DNA triplex sequence was called TRIP GFP. Controls included similar constructs with mutated cPPT or CTS and a wild type central region inserted in reverse, non-functional orientation (TRIPinv GFP). The presence of a DNA triplex in retrotranscribed TRIP GFP vector DNA, and its absence from HR GFP, TRIPinv GFP, and from vectors containing a mutated version of the central triplex sequence, was confirmed by S1 nuclease cleavage of Hirt DNA isolated from transduced cells.

The number of vector particles produced by transient transfection was normalized prior to transduction according to the levels of capsid protein (p24), reverse transcriptase activity, and the quantity of genomic vector RNA in transfected cell supernatants. Similar production of the various vectors was obtained, with a linear correlation between the three normalization criteria (data not shown). Hence insertion of the central region of the HIV-1 genome into the HR vector did not influence the rate of genomic RNA encapsidation. Dividing or non-dividing (aphidicolin treated) HeLa cells, were transduced with equivalent numbers of HR-GFP or TRIP-GFP vector particles and GFP expression was monitored 48 hours later by fluorescence quantitation. Pseudotransduction of GFP activity due to the direct delivery of GFP proteins to target cells by the fusing vector particles was calculated from the transduction of cells treated with an HIV-1 RT inhibitor (1 µM Nevirapin, Boehringer Ingelheim) and this background subtracted from the fluorescence signal. Non-specific fluorescence due to secondary transfection caused by calcium/phosphate DNA co-precipitate in the vector supernatants was eliminated by treating the vector stock with DNaseI prior to transduction.

Figure 5B:
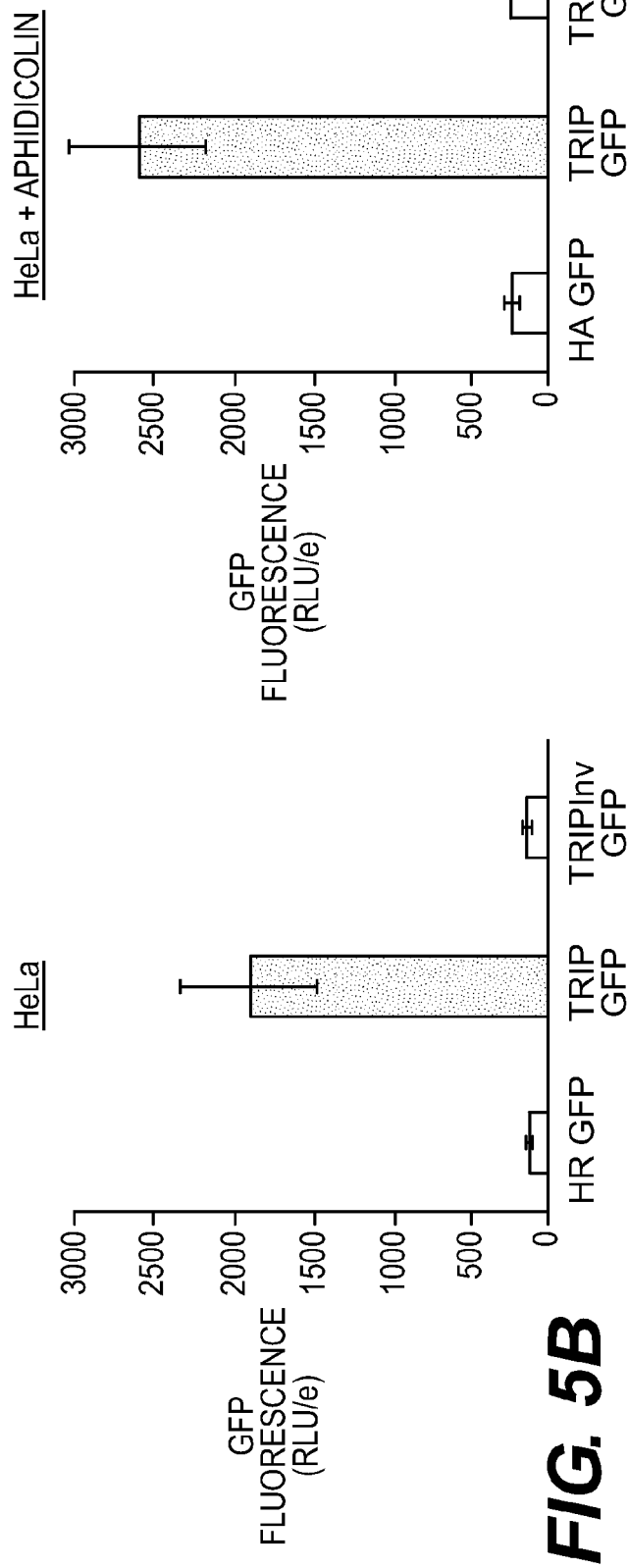

Under these conditions, the presence of the triplex sequence in the HIV vector increased GFP transduction in HeLa cells by more than ten fold (FIG. 5B). A similar enhancement of gene transduction was observed in other target cell lines such as MT4 or 293T (data not shown). This effect was lost if the triplex sequence was inserted in the reverse orientation (FIG. 5B) or mutated in the cPPT (not shown).

Example 9

The Presence of a DNA Triplex in HIV-1 Vectors Increases the Rate of Vector Genome Nuclear Import to Wild Type Levels It was then of interest to determine whether the increase in GFP fluorescence induced by insertion of a triplex sequence in the HIV vector was due to its effect on the nuclear import of vector DNA. To address this question, we adapted our quantitative Southern blot assay for intracellular viral DNA to the vector system. DNA from vector transduced cells was digested with EcoNI and AvaII to produce an internal 0.8 kb fragment, and with XhoI. Using a PCR generated DNA probe exactly overlapping the EcoNI site, signals specific for the unintegrated linear vector genome, and for one and two LTR DNA circles were expected at 1.2 kb, 1.4 kb, and 2 kb respectively. The processing of vector DNA was analyzed at various time points after transduction of HeLa cells.

Figure 5C:
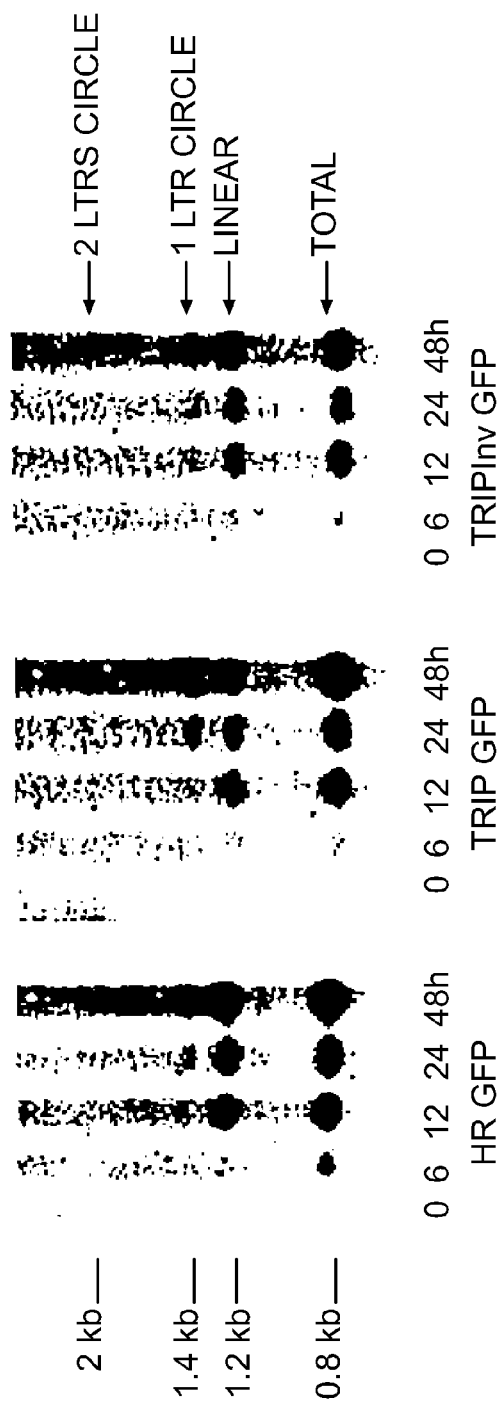
Figure 5D:
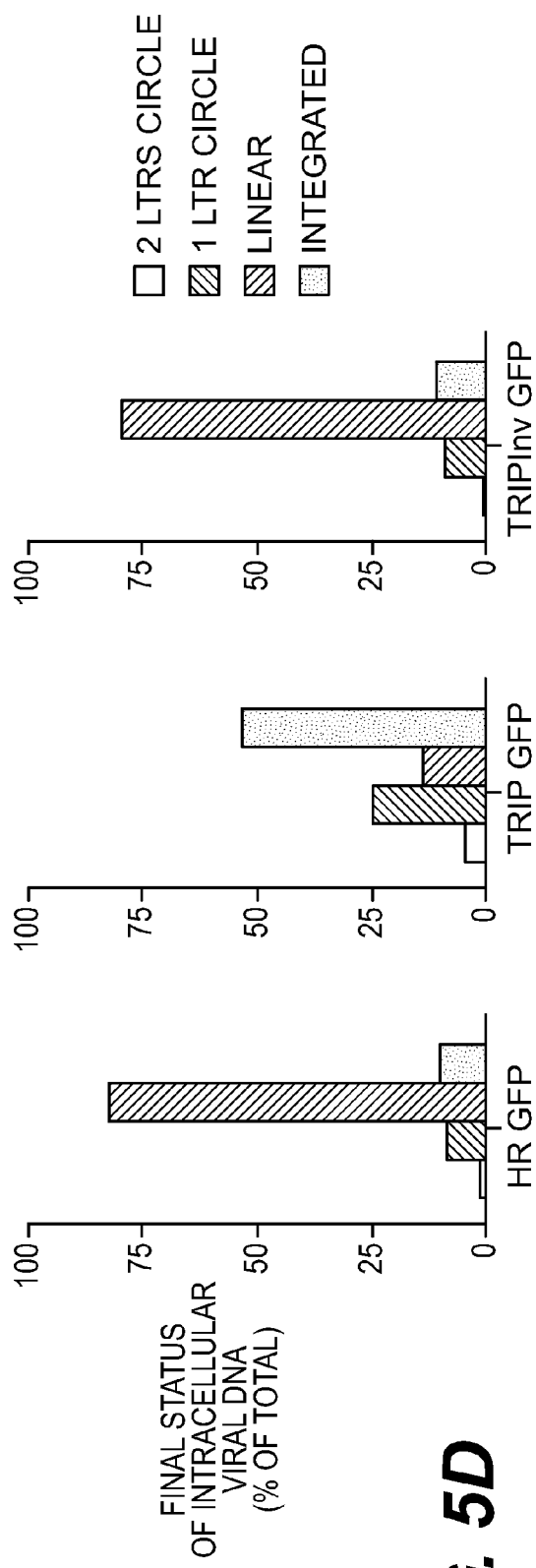

The total quantity of vector DNA synthesized in transduced cells was comparable for vectors containing or lacking the DNA triplex (FIG. 5C). Once again, insertion of the cPPT and CTS sequences, in either orientation, into the HR vector did not influence the rate of reverse transcription of its genome. After phosphorimage quantitation, we found the intracellular fate of DNA from the HR-GFP and TRIPinv-GFP vectors (FIG. 5D) to closely resemble that of DNA from central triplex defective viruses and the fate of DNA from the TRIP-GFP vector to follow that of DNA from the wild type HIV-1 LAI virus (FIG. 3C).

A defect of DNA nuclear import was evident in the case of the HR-GFP and TRIPinv-GFP vectors. The intracellular fate of DNA from these vectors was characterized by a strong accumulation of unintegrated linear molecules, together with small amounts of integrated provirus and one and two LTR circles. This DNA profile was strongly reminiscent of that of the cPPT-D mutant virus. On completion of the processing of vector DNA in transduced cells, 70 to 80% of the DNA from HR-GFP and TRIPinv-GFP constructs remained in the form of unintegrated linear molecules, while only 10 to 15% were present as unintegrated on LTR circles and 5 to 10% as integrated proviruses. This low but detectable amount of integrated vector DNA would account for the gene transduction obtained using HR-GFP or TRIPinv-GFP vectors.

This quantitative assay also showed that insertion of the triplex sequence of HIV DNA into the HR vector in the correct orientation complemented its nuclear import deficiency to wild-type levels. The final state of TRIP-GFP DNA in transduced cells was similar to that observed with wild type HIV-1 virus: 50% or more of the vector DNA integrated the chromatin of the target cell, an important fraction circularized and a few molecules remained as unintegrated linear DNA (compare FIGS. 5D and 3C). By contrast, insertion of the triplex sequence into the HR vector upstream of the internal CMV promoter did not influence GFP expression at the transcriptional level. This was checked by transfection of HeLa cells with pHR-GFP, pTRIP-GFP, and pTRIPinv-GFP plasmids and fluorescence quantitation (data not shown).

It may be inferred from these results that the increase in GFP transduction obtained with the TRIP-GFP vector is entirely imputable to strong stimulation of its nuclear import by the presence of the triplex. This finding again emphasizes the important role of the HIV DNA triplex in the nuclear import of viral and vector DNA.

Example 10

Figure 7A:
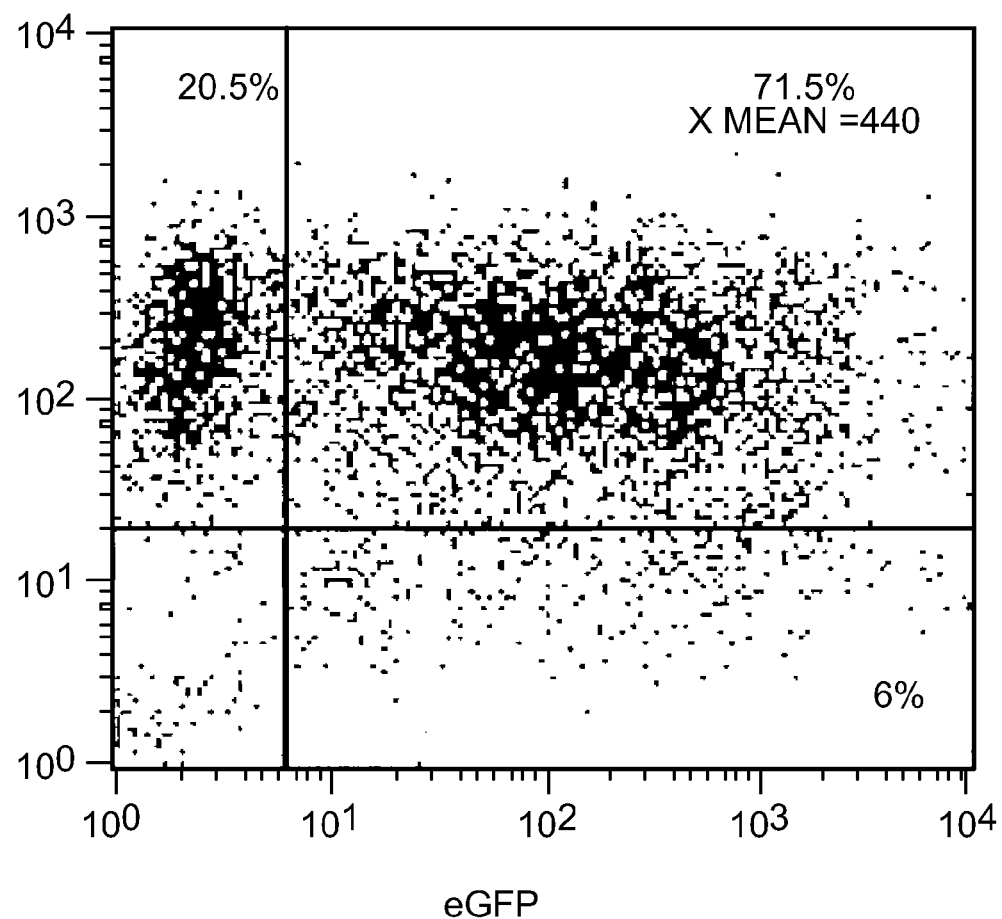
Figure 7B:
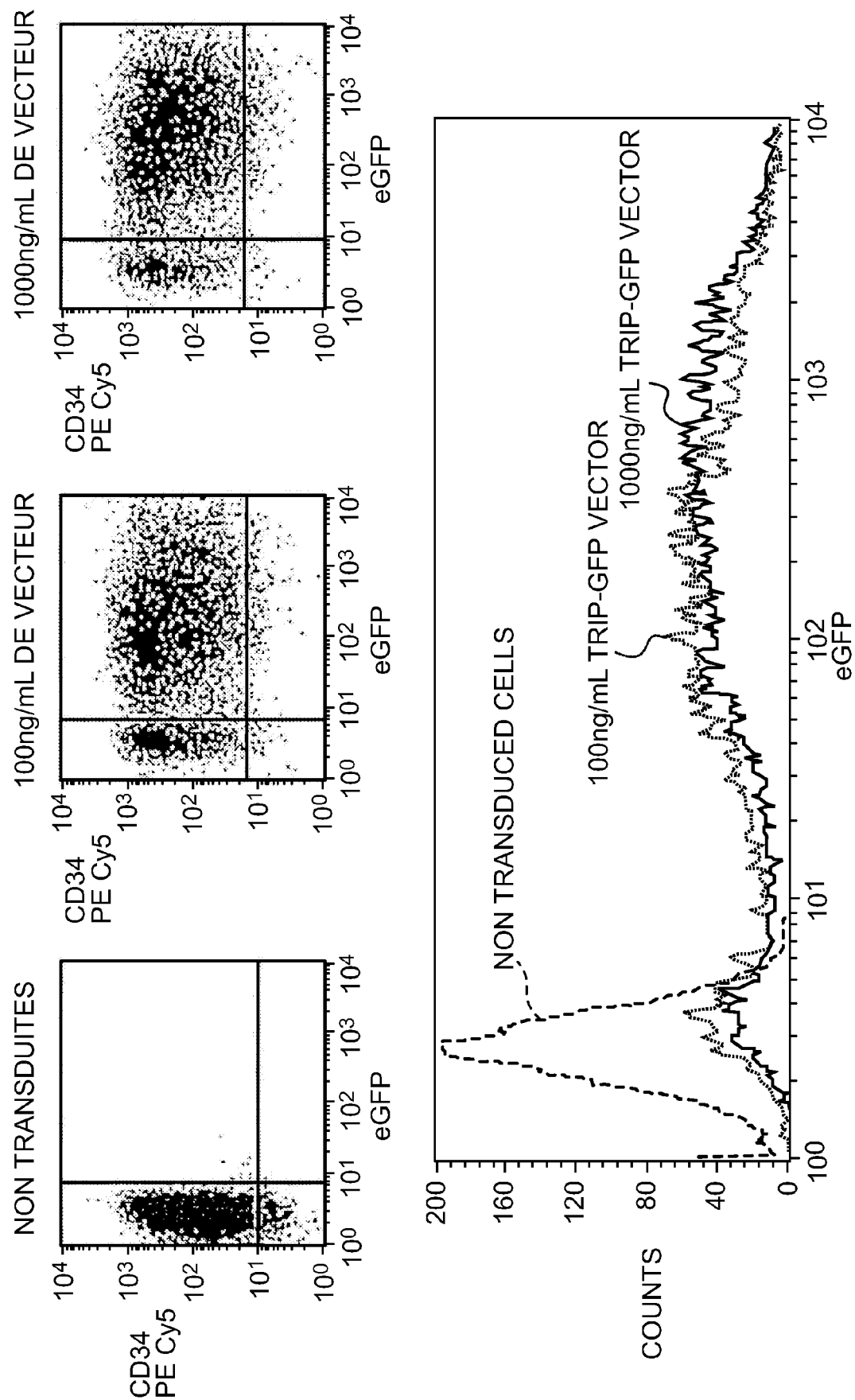

HIV-1 Vectors Containing the DNA Triplex Sequence Allow an Efficient Gene Transfer in Hematopoietic Stem Cells FIGS. 7A and 7B illustrate the results of two successful transduction experiments using CD34+ human cord blood cells. They show that after a short 24 or 60 hour transduction protocol, respectively 71.5% and more than 90% of the CD34+ cells strongly express the GFP reporter protein. This expression reflects stable transduction of the cells since viral integration was confirmed, at least in the same proportions, by PCR assays on DNA extracted from progenitor-derived cell colonies harvested 14 days after having seeded cells in clonogenic progenitor assay. Identical results have been obtained using freshly purified CD34+ cells or the same CD34+ cells that have been frozen after purification and thawed several weeks later for the transduction experiment. We also had comparable transduction efficiencies using another hematopoietic stem cell source, peripheral blood mobilized stem cells (PBMC), collected by cytapheresis after cytokine stimulation. CD34+ PBMC were also transduced either immediately after purification or after a freezing/thawing step with identical results. Using long term culture (LTC) and NOD-SCID repopulating assays we have shown that we have transduced cells having multiple lympho-myeloid potentialities and the ability to repopulate NOD-SCID mouse bone marrow 4 moths after graft. These functional assays represent the ultimate experiments available, at the moment, to assess human hematopoietic stem cell function.

Example 11

The Presence of the DNA Triplex Sequence in Lentiviral Vector Constructs Strongly Stimulates Gene Transfer into Hematopoietic Stem Cells The dose/response experiment reported in FIG. 8 (representative of 3 experiments) was designed to compare transduction efficiency in human hematopoietic stem cells of HIV-1 vectors including or lacking the DNA triplex sequence. We first plotted (A) the percentage of CD34+eGFP+ cells obtained as a function of the vector concentration used for transduction. We observe that whatever was the dose of vector, the TRIP+ vector was more efficient than the TRIP– one, with respectively a mean of 40±19% and 15.4±12.5% of CD34+ cells being eGFP+ for 500 ng viral P24/ml of each vector (n=3 exp). A 4-6 fold increase in the final percentage of GFP+ cells was obtained after transduction by the TRIP-GFP vector when compared to results obtained after transduction with HR-GFP vector. The difference in efficiency between the two vectors is also highlighted when the mean of fluorescence intensity is plotted function of the dose of virus. A plateau is reached for the TRIP– (HR-GFP) vector at dose of 100 ng P24/ml whereas fluorescence intensity in transduced cells increases with the dose of TRIP+ vector. This could reflect the limitation in nuclear import of the pre-integrative forms of the TRIP– vector and the increasing number of integrated copies per cell after transduction with increasing doses of the TRIP-GFP vector. The third plot integrates both aspects and shows the resulting effect of the DNA triplex sequence on GFP fluorescence activity in human HSC. As shown, the presence of the DNA triplex sequence in the HIV vector induce an increased GFP production in HSC by a factor of more than a ten fold.

Example 12

A Fraction of Integrated Copies of HIV Vector Genomes Remains Silent in Human Hematopoietic Transduced Cells It is possible that inactivation of the integrated transgene can occur. The transfer efficiency was always better when it is evaluated by the percentage of transduced progenitor-derived cell colonies determined by PCR assay for the integrated lentiviral vector rather than when it is evaluated by the percentage of CD34+/eGFP+ cells determined by FACS analysis 48 hours after the end of the transduction protocol. This reflects the occurrence of transcriptionally inactive proviruses either due to their integration site or to the progressive and random inactivation of the provirus while the cells proliferate and differentiate. We have observed colonies derived from a single myeloid clonogenic progenitor that some of the subclones could be GFP bright whereas others were negative, reflecting the random transcriptional inactivation of the integrated transgene in this phenotypically homogenous clonal progeny.

Example 13

Figure 9A:
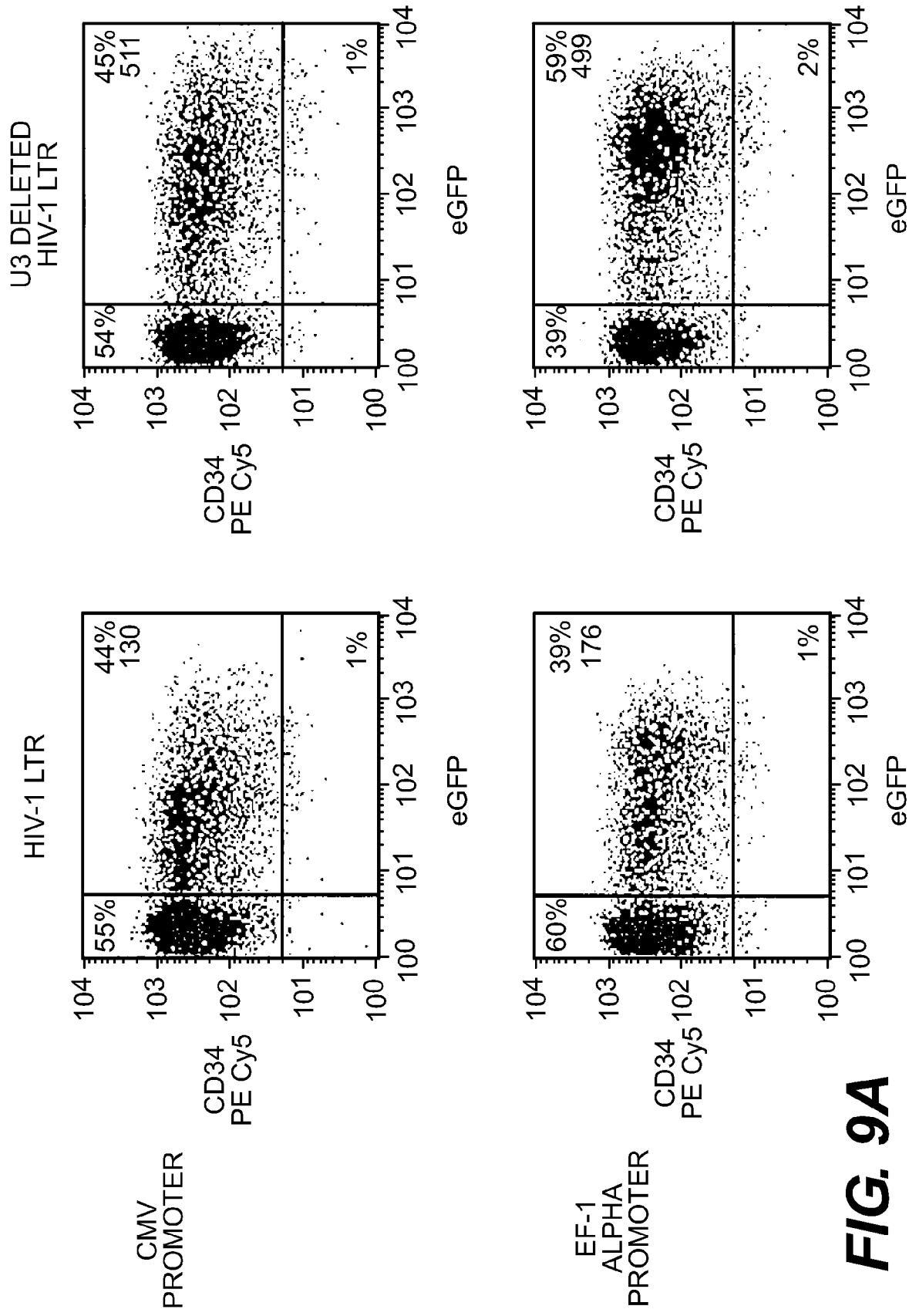
Figure 9B:
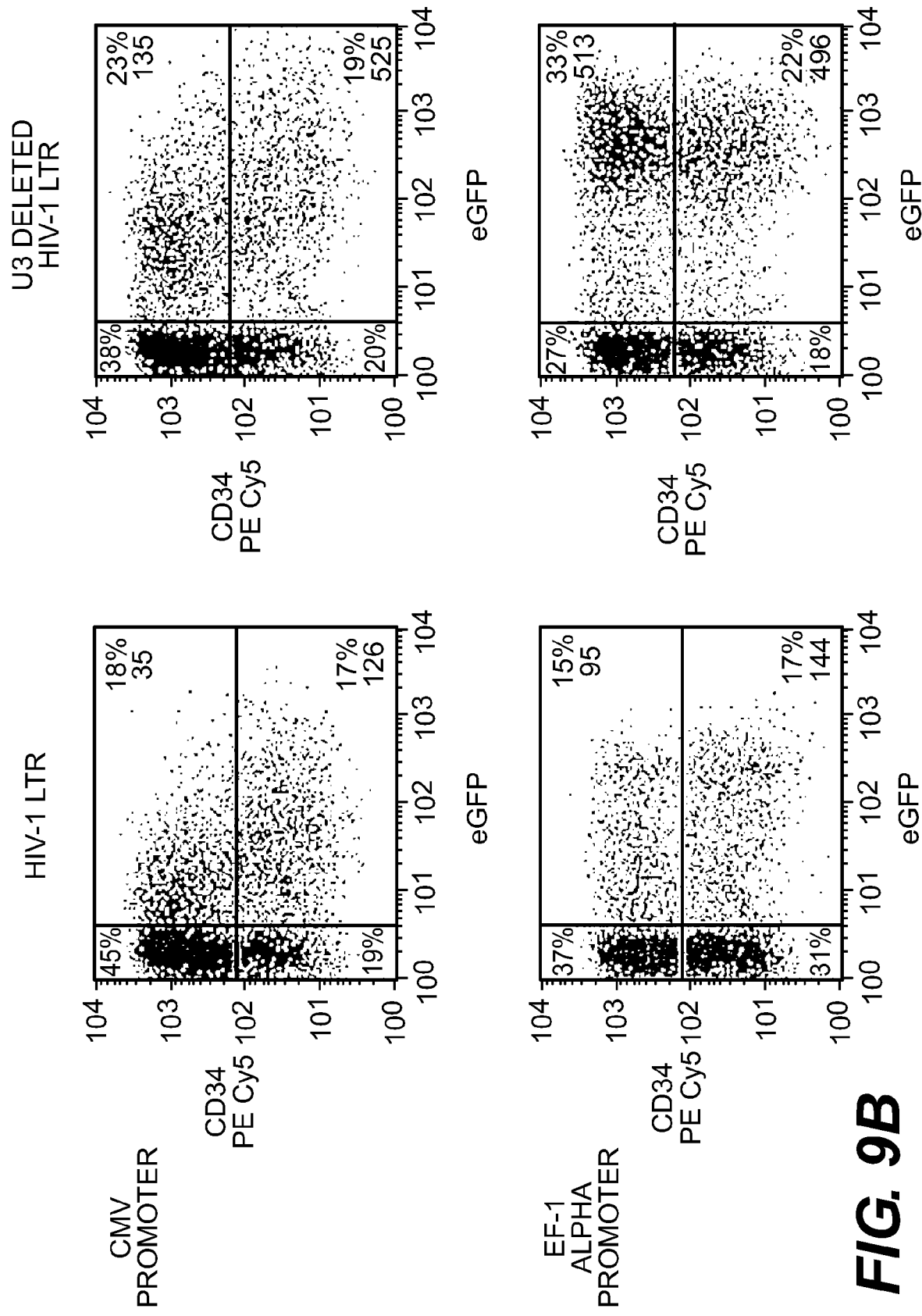

HIV Vector Containing a Deleted Version of the U3 Region of the LTR and an Internal EF1α are More Potent Systems for the Transduction of Hematopoietic Stem Cells In FIG. 9, we compared the ability of various HIV-1 derived vectors, including the DNA triplex sequence, to transduce human cord blood CD34+ cells. The effect of deletion of most of the U3 region of the 3' LTR on GFP transduction and expression in CD34+ cells was analyzed. The comparison of vectors containing an intact HIV-1 LTR or a U3 deleted version was conducted in the context of a CMV internal promoter or an EF1α internal promoter (Kim et al., 1990) to drive the expression of the GFP reporter gene. All transduction experiments were conducted using the same concentration of vector particles (500 ng P24/ml) after normalization of vector stocks using a commercially available ELISA assay for the P24 (Capsid protein) HIV-1 antigen (Dupont). Flow cytometry analysis (FACS) were performed either at 48 hours (FIG. 9A) or 120 hours (FIG. 9B) after the 24 hour transduction period.

Interestingly, deletion of the U3 region of the LTR in HIV-1 vectors induced a slight increase in the percentage of GFP positive cells in all cases. This increase was modest when analyzed at 48 hours. At this time, a pseudotransduction mechanism might be responsible for a fraction of the GFP positive cells. Pseudotransduction is the direct delivery of GFP proteins to target cells by the fusing retroviral vector particle, without the need for an actual integration of the retroviral vector genome. The increase in the percentage of GFP positive after transduction by the U3 deleted versions of the HIV-1 vectors became more evident at 120 hours after transduction (FIG. 9B). At this time, up to a two fold increase in the percentage of GFP positive cells is seen after transduction by the TRIP ΔU3-EF1α-GFP vector when compared to the results obtained with the equivalent vector but containing an intact HIV-1 LTR. More importantly, deletion of the U3 region of the HIV-1 LTR in the HIV-1 triplex vectors induced a better expression of the GFP reporter protein. The mean of fluorescence intensity in transduced human HSC when analyzed by FACS was always superior of a three to five fold factor in the case of the U3 deleted versions than with vectors containing an intact HIV-1 LTR. This benefit of GFP expression was observed whether the CMV or the EF1α promoters where used as an internal promoter in the HIV-1 vector construct. The molecular mechanism explaining this enhanced expression of GFP proteins in transduced cells is not known. Some sequence in the HIV-1 LTR may negatively influence the expression driven by the internal promoter. Alternatively, a basal transcription initiated at the HIV-1 LTR may interfere with the initiation of transcription at the internal promoter.

This study also shows that the EF1α promoter is a better promoter in human HSC than the CMV promoter. In FIG. 9B, the mean of GFP fluorescence intensity is three to five times better in the case of the EF1α promoter than in the case of the CMV promoter.

It will be apparent to those skilled in the art that various modifications and variations can be made in the practice of the present invention without departing from the scope or spirit of the invention.

REFERENCES

All references cited herein are hereby incorporated in their entireties by reference.

Barbosa, P., Charneau, P., Dumey, N., and Clavel, F. (1994). Kinetic analysis of HIV-1 early replicative steps in a coculture system. AIDS Research & Human Retroviruses. 10, 53-59.

Bormerot, C., Rocancourt, D., Briand, P., Grimber, G., and Nicolas, J. (1987). A beta-galactosidase hybrid protein targeted to nuclei as a marker for development studies. Proc. Natl. Acad. of Sci. USA 84, 6795-9.

Borroto-Esoda, K., and Boone, L. (1991). Equine infectious anemia virus and human immunodeficiency virus DNA synthesis in vitro: characterization of the endogenous reverse transcriptase reaction. Journal of Virology 65, 1952-1959.

Bowerman, B., Brown, P., Bishop, J., and Varmus, H. (1989). A nucleoprotein complex mediates the integration of retroviral DNA. Genes and Development 3, 469-78.

Bukrinskaya, A., Brichacek, B., Mann, A., and Stevenson, M. (1998). Establishment of a functional human immunodeficiency virus type 1 (HIV-1) reverse transcription complex involves the cytoskeleton. Journal of Experimental Medicine 188, 2113-25.

Bukrinsky, M. I., Sharova, N., Dempsey, M. P., Stanwick, T. L., Bukrinskaya, A. G., Haggerty, S., and Stevenson, M. (1992). Active nuclear import of human immunodeficiency virus type 1 preintegration complexes. Proc Natl Acad Sci 89, 6580-6584.

Bukrinsky, M., Sharova, N., McDonald, T., Pushkarskaya, T., Tarpley, W., and Stevenson, M. (1993a). Association of integrase, matrix, and reverse transcriptase antigens of human immunodeficiency virus type 1 with viral nucleic acids following acute infection. Proc. Natl. Acad. of Sci. USA 90, 6125-9.

Bukrinsky, M. I., Haggerty, S., Dempsey, M. P., Sharova, N., Adzhubel, A., Spitz, L., Lewis, P., Goldfarb, D., Emerman, M. and Stevenson M (1993b). A nuclear localization signal within HIV-1 matrix protein that governs infection of nondividing cells. Nature 365, 666-669.

Case S S. Price M A. Jordan C T. Yu X J. Wang L. Bauer G. Haas D L. Xu D. Stripecke R. Naldini L. Kohn D B. Crooks G M. Stable transduction of quiescent CD34(+)CD38(−) human hematopoietic cells by HIV-1-based lentiviral vectors. Proceedings of the National Academy of Sciences of the United States of America. 96(6):2988-93, 1999.

Charneau, P., and Clavel, F. (1991). A single-stranded gap in human immunodeficiency virus unintegrated linear DNA defined by a central copy of the polypurine tract. Journal of Virology 65, 2415-2421.

Charneau, P., Alizon, M., and Clavel, F. (1992). A second origin of plus strand synthesis is required for optimal HIV replication. Journal of Virology 66, 2814-2820.

Charneau, P., Mirambeau, G., Roux, P., Paulous, S., Buc, H., and Clavel, F. (1994). HIV-1 reverse transcription: a termination step at the center of the genome. Journal of Molecular Biology 241, 651-662.

Croisille, L. et al. (1994). Hydrocortisone differentially affects the ability of murine stromal cells and human marrow-derived adherent cells to promote the differentiation of Cd34++/CD38-long-term culture-initiating cells. Blood 84: 4116-4124.

Dworetzky, S., Lanford, R., and Feldherr, C. (1988). The effects of variations in the number and sequence of targeting signals on nuclear uptake. Journal of Cell Biology 107, 1279-87.

Emerman, M., Bukrinski, M., and Stevenson, M. (1994). HIV-1 infection of non-dividing cells, reply to Freed E O and Martin M A. Nature 369, 108.

Evans et al., (Jun. 10, 1999). Hum Gene Therapy 10(9):1479-89.

Farnet, C., and Haseltine, W. (1990). Integration of human immunodeficiency virus type 1 DNA in vitro. Proc. Natl. Acad. of Sci. USA 87, 4164-8.

Fouchier, R. A., Meyer, B. E., Simon, J. H. Fischer, U., and Malim, M. H. (1997). HIV-1 infection of non-dividing cells: evidence that the amino-terminal basic region of the viral matrix protein is important for Gag processing but not for post-entry nuclear import. EMBO Journal 16, 4531-4539.

Freed, E. O., and Martin, M. A. (1994). HIV-1 infection of non-dividing cells. *Nature* 369, 107-108.

Freed, E. O., Englund, G., and Martin, M. A. (1995). Role of the basic domain of human immunodeficiency virus type 1 matrix in macrophage infection. Journal of Virology 69, 3949-3954.

Freed, E. O., Englund, G., Maldarelli, F., and Martin, M. A. (1997). Phosphorylation of residue 131 of HIV-1 matrix is not required for macrophage infection. Cell 88, 171-173.

Gallay, P., Swingler, S., Aiken, C., and Trono, D. (1995a). HIV-1 infection of non dividing cells: C-terminal tyrosine phosphorylation of the viral matrix protein as a key regulator. *Cell* 80, 379-388.

Gallay, P., Swingler, S., Song, J., Bushman, F., and Trono, D. (1995b) HIV nuclear import is governed by the phosphotyrosine-mediated binding of matrix to the core domain of integrase. *Cell* 83, 569-576.

Gallay, P., Hope, T., Chin, D., and Trono, D. (1997). HIV-1 infection of nondividing cells through the recognition of integrase by the importin/karyopherin pathway. Proc. Natl. Acad. of Sci. USA 94, 9825-9830.

Gartner, S., Markovits, P., Marcovitz, D. M., Kaplan, M. H., Gallo, R. C., and Popovic, M. (1986). The role of mononuclear phagocytes in HTLV-III/LAV infection. *Science* 233, 215-219.

Gelderblom, H. (1991). Assembly and morphology of HIV: potential effect of structure on viral function. AIDS 5, 617-37.

Gulizia, J., Dempsey, M., Sharova, N., Bukrinsky, M., Spitz, L., Goldfarb, D., and Stevenson, M. (1994). Reduced nuclear import of human immunodeficiency virus type 1 preintegration complexes in the presence of a prototypic nuclear targeting signal. Journal of Virology 68, 2021-5.

Hagstrom, J., Ludtke, J., Bassik, M., Sebestyen, M., Adam, S., and Wolff, J. (1997). Nuclear import of DNA in digitonin-permeabilized cells. Journal of Cell Science 110, 2323-31:

Hamm, J., and Mattaj, I. (1990). Monomethylated cap structures facilitate RNA export from the nucleus. Cell 63, 109-18.

Harada, S., Koyanagi, Y., and Yamamoto, N. (1985). Infection of HTLV-III/LAV in HTLV-I-carrying cells MT-2 and MT-4 and application in a plaque assay. Science 229, 563-6.

Harris, J. D., Scott, J. V., Traynor, B., Brahic, M., Stowring, L., Ventura, P., Haase, A. T., and Peluso, R. (1981). Visna virus DNA: discovery of a novel gapped structure. Virology, 573-583.

Heinzinger, N., Bukinsky, M., Haggerty, S., Ragland, A., Kewalramani, V., Lee, M., Gendelman, H., Ratner, L., Stevenson, M., and Emerman, M. (1994). The Vpr protein of human immunodeficiency virus type 1 influences nuclear localization of viral nucleic acids in nondividing host cells. Proc. Natl. Acad. of Sci. USA 91, 7311-5.

Ho, D., Rota, T., and Hirsch, M. (1986). Infection of monocyte/macrophages by human T lymphotropic virus type III. Journal of Clinical Investigation 77, 1712-1715.

Huber, H. E., and Richardson, C. C. (1990). Processing of the primer for plus strand DNA synthesis by human immunodeficiency virus 1 reverse transcriptase. Journal of Biological Chemistry 265, 10565-10573.

Hungnes, O., Tjotta, E., and Grinde, B. (1992) Mutations in the central polypurine tract of HIV-1 result in delayed replication. Virology 190, 440-2.

Issaad, C. et al. (1993). A murine stromal cell line allows the proliferation of very primitive humain CD34++/CD38-progenitor cells in long-term cultures and semisolid assays. Blood Vol. 81, No 11: pp 2916-2924.

Kalderon, D., Roberts, B., Richardson, W., and Smith, A. (1984). A short amino acid sequence able to specify nuclear location. Cell 39, 499-509.

Karageorgos, L., Li, P., and Burrel, C. (1993). Characterisation of HIV replication complexes early after cell to cell infection. *AIDS Res Hum Retroviruses* 9, 817-823.

Kim D W, Uetsuki T, Kaziro Y, Yamaguchi N, Sugano S. Use of the human elongation factor 1 alpha promoter as a versatile and efficient expression system. Gene, 1990, 91: 217-223.

Klarmann, G., Schauber, C., and Preston, B. (1993). Template-directed pausing of DNA synthesis by HIV-1 reverse transcriptase during polymerization of HIV-1 sequences in vitro. Journal of Biological Chemistry. 268, 9793-802.

Koostra, N., and Schuitemaker, H. (1999). Phenotype of HIV-1 lacking a functional nuclear localization signal in matrix protein of gag and Vpr is comparable to wild-type HIV-1 in primary macrophages. Virology 253, 170-80.

Kunkel, T. (1985). Rapid and efficient site-specific mutagenesis without phenotypic selection. Proc. Natl. Acad. of Sci. USA 82, 488-92.

Lanford, R., and Butel, J. (1984). Construction and characterization of an SV40 mutant defective in nuclear transport of T antigen. Cell 37, 801-13.

Lavigne, M., Roux, P., Buc, H., and Schaeffer, F. (1997). DNA curvature controls termination of plus strand DNA synthesis at the centre of HIV-1 genome. Journal of Molecular Biology 266, 507-524.

Lewis, P., Hensel, M., and Emerman, M. (1992). Human immunodeficiency virus infection of cells arrested in the cell cycle. EMBO Journal 11, 3053-3058.

Lori, F., di Marzo Veronese, F., de Vico, A., Lusso, P., Reitz, M. J., and Gallo, R. (1992). Viral DNA carried by human immunodeficiency virus type 1 virions. J. Virol. 66, 5067-5074.

Miller, M., Farnet, C., and Bushman, F. (1997). Human immunodeficiency virus type 1 preintegration complexes: studies of organization and composition. Journal of Virology 71, 5382-90.

Miyoshi H. Smith K A. Mosier D E. Verma I M. Torbett B E. (Jan. 29, 1999). Transduction of human CD34+ cells that mediate long-term engraftment of NOD/SCID mice by HIV vectors. Science 283(5402):682-6.

Naldini, L., Blomer, U., Gallay, P., Ory, D., Mulligan, R., Gage, F., Verma, I., and Trono, D. (1996). In vivo gene delivery and stable transduction of nondividing cells by a lentiviral vector. Science 272, 263-7.

Panet, A., Baltimore, D., and Hanafusa, H. (1975). Quantitation of avian RNA tumor virus reverse transcriptase by radioimmunoassay. J. Virol. 16, 146-152.

Pflumio, F. et al. (1996). Phenotype and function of human hematopoietic cells engrafting immune-deficient CB 17-severe combined immunodeficiency mice and non-obese diabetic-severe combined immunodeficiency mice after transplantation of human cord blood mononuclear cells. Blood 88: 3731-3740.

Popov, S., Rexach, M., Zybarth, G., Reiling, N., Lee, M. A., Ratner, L., Lane, C. M., Moore, M. S., Blobel, G., and Bukrinsky, M. (1998). Viral protein R regulates nuclear import of the HIV-1 pre-integration complex. EMBO Journal 17, 909-917.

Poznansky, M., Lever, A., Bergeron, L., Haseltine, W., and Sodroski, J. (1991). Gene transfer into human lymphocytes by a defective human immunodeficiency virus type 1 vector. Journal of Virology 65, 532-6.

Robin, C. et al. (1999). Identification of T-lymphoid progenitor cells in CD34+CD38low and CD34+CD38+ subsets of human cord blood and bone marrow cells using NOD-SCID fetal thymus organ cultures. Br J Haematol 104: 809-819.

Roe, T. Y., Reynolds, T. C., Yu, G., and Brown, P. O. (1993). Integration of murine leukemia virus DNA depends on mitosis. *EMBO J* 12, 2099-2108.

Stetor, S., Rausch, J., Guo, M., Burnham, J., Boone, L., Waring, M., and Le Grice, S. (1999). Characterization of (+) strand initiation and termination sequences located at the center of the equine infectious anemia virus genome. Biochemistry 38, 3656-67.

Thormar, H. (1963). The growth cycle of Visna virus in monolayer cultures of sheep cells. *Virology* 19, 273-278.

Uchida et al. (Sep. 29, 1998). PNAS USA 95(20):11939-44.

von Schwedler, U., Kornbluth, R., and Trono, D. (1994). The nuclear localization signal of the matrix protein of human immunodeficiency virus type 1 allows the establishment of infection in macrophages and quiescent T lymphocytes. Proc. Natl. Acad. of Sci. USA 91, 6992-6.

Weinberg, J. B., Matthews, T. J., Cullen, B. R., and Malim, M. H. (1991). Productive human immunodeficiency virus type 1 (HIV-1) infection of nonproliferating human monocytes. Journal of Experimental Medicine 174, 1477-1482.

Whittaker, G., and Helenius, A. (1998). Nuclear import and export of viruses and virus genomes. Virology 246, 1-23.

Yee, J., Miyanohara, A., LaPorte, P., Bouic, K. Burns, J., and Friedmann, T. (1994). A general method for the generation of high-titer, pantropic retroviral vectors: highly efficient infection of primary hepatocytes. Proc. Natl. Acad. of Sci. USA 91, 9564-8.

What is claimed is:

1. A recombinant lentiviral vector particle comprising Gag, Pol, and Env proteins and a replication-deficient lentiviral vector comprising:
   (a) at least one copy of the cPPT and CTS cis-acting regions of a retrovirus, wherein said cPPT and CTS regions induce a three-stranded DNA structure upon reverse transcription,
   (b) a transgene of interest, and
   (c) a deletion of the promoter and the enhancer sequences of U3 region of the HIV-1 LTR.

2. The lentiviral vector particle of claim 1, wherein the cis-acting central initiation region and the cis-acting termination region are derived from a human immunodeficiency virus type 1 genome.

3. The lentiviral vector particle of claim 1, wherein the transcription of the transgene is controlled by non-retroviral sequences.

4. The lentiviral vector particle of claim 3, wherein the transcription of the transgene is controlled by a cytomegalovirus promoter.

5. The lentiviral vector particle of claim 3, wherein the transcription of the transgene is controlled by a phosphoglycerate kinase promoter.

6. The lentiviral vector particle of claim 3, wherein the transcription of the transgene is controlled by an elongation factor 1α (EF1α) promoter.

7. The lentiviral vector particle of claim 1, wherein the recombinant vector particle comprises human immunodeficiency virus type 1 Gag, Pol, and Env proteins.

8. The lentiviral vector particle of claim 1, wherein the recombinant vector particle comprises human immunodeficiency virus type 1 Gag and Pol proteins, and vesicular somatitis virus Env proteins.

9. The lentiviral vector particle of claim 2, wherein the transcription of the transgene is controlled by non-retroviral sequences.

10. The lentiviral vector particle of claim 9, wherein the transcription of the transgene is controlled by a cytomegalovirus promoter.

11. The lentiviral vector particle of claim 9, wherein the transcription of the transgene is controlled by a phosphoglycerate kinase promoter.

12. The lentiviral vector particle of claim 9, wherein the transcription of the transgene is controlled by an elongation factor 1α (EF1α) promoter.

13. The lentiviral vector particle of claim 2, wherein the recombinant vector particle comprises human immunodeficiency virus type 1 Gag, Pol, and Env proteins.

14. The lentiviral vector particle of claim 2, wherein the recombinant vector particle comprises human immunodeficiency virus type 1 Gag and Pol proteins, and vesicular stomatitis virus Env proteins.

15. A method for the preparation of a recombinant cell comprising transducing a host cell with the lentiviral vector particle of claim 1.

16. The method of claim 15, wherein the host cell is a eukaryotic cell.

17. The method of claim 15, wherein the host cell is a dividing cell.

18. The method of claim 15, wherein the host cell is a non-dividing cell.

19. The method of claim 15, wherein the host cell is a hematopoietic cell.

20. The method of claim 15, wherein the host cell is a stem cell.

* * * * *